US010912862B2

(12) United States Patent
Mauney et al.

(10) Patent No.: US 10,912,862 B2
(45) Date of Patent: Feb. 9, 2021

(54) MULTI-LAYER BIOMATERIAL FOR TISSUE REGENERATION AND WOUND HEALING

(71) Applicants: Children's Medical Center Corporation, Boston, MA (US); Tufts University, Medford, MA (US)

(72) Inventors: Joshua R. Mauney, Watertown, MA (US); Carlos R. Estrada, Brookline, MA (US); David L. Kaplan, Concord, MA (US); Eun Seok Gil, Lexington, MA (US)

(73) Assignees: Children's Medical Center Corporation, Boston, MA (US); Tufts University, Medford, MA (US)

( * ) Notice: Subject to any disclaimer, the term of this patent is extended or adjusted under 35 U.S.C. 154(b) by 0 days.

(21) Appl. No.: 14/377,128

(22) PCT Filed: Feb. 5, 2013

(86) PCT No.: PCT/US2013/024744
§ 371 (c)(1),
(2) Date: Aug. 6, 2014

(87) PCT Pub. No.: WO2013/119551
PCT Pub. Date: Aug. 15, 2013

(65) Prior Publication Data
US 2015/0086605 A1 Mar. 26, 2015

Related U.S. Application Data

(60) Provisional application No. 61/595,233, filed on Feb. 6, 2012.

(51) Int. Cl.
| | | |
|---|---|---|
| *A61L 27/58* | (2006.01) | |
| *A61L 27/22* | (2006.01) | |
| *A61L 27/36* | (2006.01) | |
| *B29C 39/00* | (2006.01) | |
| *A61L 27/54* | (2006.01) | |
| *A61L 27/56* | (2006.01) | |
| *A61L 27/38* | (2006.01) | |
| *B29L 31/00* | (2006.01) | |

(52) U.S. Cl.
CPC ......... *A61L 27/227* (2013.01); *A61L 27/3604* (2013.01); *A61L 27/3834* (2013.01); *A61L 27/54* (2013.01); *A61L 27/56* (2013.01); *A61L 27/58* (2013.01); *B29C 39/003* (2013.01); *A61L 2300/22* (2013.01); *A61L 2300/254* (2013.01); *A61L 2300/256* (2013.01); *A61L 2300/258* (2013.01); *A61L 2300/406* (2013.01); *A61L 2300/41* (2013.01); *A61L 2300/412* (2013.01); *A61L 2300/414* (2013.01); *A61L 2300/43* (2013.01); *A61L 2300/608* (2013.01); *A61L 2430/22* (2013.01); *B29L 2031/755* (2013.01); *B29L 2031/7532* (2013.01)

(58) Field of Classification Search
None
See application file for complete search history.

(56) References Cited

U.S. PATENT DOCUMENTS

| | | | |
|---|---|---|---|
| 4,233,212 A | 11/1980 | Otoi et al. | |
| 4,820,418 A | 4/1989 | Hirotsu et al. | |
| 5,047,507 A | 9/1991 | Buchegger et al. | |
| 5,245,012 A | 9/1993 | Lombari et al. | |
| 5,252,277 A | 10/1993 | Uy | |
| 5,290,494 A | 3/1994 | Coombes et al. | |
| 5,606,019 A | 2/1997 | Cappello | |
| 5,728,810 A | 3/1998 | Lewis et al. | |
| 5,770,193 A | 6/1998 | Vacanti et al. | |
| 5,994,099 A | 11/1999 | Lewis et al. | |
| 6,004,667 A * | 12/1999 | Sakurada | A01N 59/16 428/323 |
| 6,110,590 A | 8/2000 | Zarkoob et al. | |
| 6,123,819 A | 9/2000 | Peeters | |
| 6,175,053 B1 | 1/2001 | Tsubouchi | |
| 6,592,623 B1 | 7/2003 | Bowlin et al. | |
| 6,815,427 B2 | 11/2004 | Tsubouchi et al. | |
| 6,902,932 B2 | 6/2005 | Altman et al. | |
| 7,041,797 B2 | 5/2006 | Vollrath | |
| 7,057,023 B2 | 6/2006 | Islam et al. | |
| 7,285,637 B2 | 10/2007 | Armato et al. | |
| 7,635,755 B2 | 12/2009 | Kaplan et al. | |
| 7,662,409 B2 | 2/2010 | Masters | |
| 7,674,882 B2 | 3/2010 | Kaplan et al. | |
| 7,727,575 B2 | 6/2010 | Kaplan et al. | |
| 7,842,780 B2 | 11/2010 | Kaplan et al. | |

(Continued)

FOREIGN PATENT DOCUMENTS

| | | |
|---|---|---|
| CA | 2405850 A1 | 10/2002 |
| EP | 1440088 A2 | 7/2004 |

(Continued)

OTHER PUBLICATIONS

Lovett et al; Biomaterials. Dec. 2007; 28(35): 5271-5279.*
Jin et al.; Biomacromolecules 2004, 5, 711-717; published online Jan. 23, 2004.*
Corpas et al.; Methods in Enzymology; vol. 437; Ch. 28, pp. 561-574, published 2008.*
U.S. Appl. No. 61/224,618, dated Jul. 10, 2009, Numata et al.
Abrams, P., Describing bladder storage function: overactive bladder syndrome and detrusor overactivity, Urology, 62(5 Suppl 2):28-37 (2003).

(Continued)

*Primary Examiner* — Jeffrey T. Palenik
(74) *Attorney, Agent, or Firm* — Quarles & Brady LLP

(57) ABSTRACT

The technology described herein is directed to compositions comprising at least a first porous biomaterial layer and a second impermeable biomaterial layer and methods relating thereto. In some embodiments, the compositions and methods described herein relate to wound healing, e.g. repair of wounds and/or tissue defects.

29 Claims, 18 Drawing Sheets

(56) References Cited

U.S. PATENT DOCUMENTS

| | | |
|---|---|---|
| 7,960,509 B2 | 6/2011 | Kaplan et al. |
| 8,071,722 B2 | 12/2011 | Kaplan et al. |
| 8,172,901 B2 | 5/2012 | Altman et al. |
| 8,501,172 B2 | 8/2013 | Kaplan et al. |
| 2002/0028243 A1 | 3/2002 | Masters |
| 2003/0007991 A1 | 1/2003 | Masters |
| 2003/0099630 A1 | 5/2003 | DiBenedetto et al. |
| 2003/0114917 A1 | 6/2003 | Holloway et al. |
| 2003/0183978 A1 | 10/2003 | Asakura |
| 2004/0005363 A1 | 1/2004 | Tsukada et al. |
| 2004/0266992 A1 | 12/2004 | Migliaresi et al. |
| 2005/0260706 A1 | 11/2005 | Kaplan et al. |
| 2005/0283256 A1 | 12/2005 | Sommerich et al. |
| 2007/0187862 A1 | 8/2007 | Kaplan et al. |
| 2007/0212730 A1 | 9/2007 | Vepari et al. |
| 2008/0085272 A1 | 4/2008 | Kaplan et al. |
| 2008/0147197 A1 | 6/2008 | McKay |
| 2008/0249452 A1 | 10/2008 | Tanaka et al. |
| 2008/0293919 A1 | 11/2008 | Kaplan et al. |
| 2009/0202614 A1 | 8/2009 | Kaplan et al. |
| 2009/0232963 A1 | 9/2009 | Kaplan et al. |
| 2009/0234026 A1 | 9/2009 | Kaplan et al. |
| 2010/0028451 A1 | 2/2010 | Kaplan et al. |
| 2010/0046902 A1 | 2/2010 | Kaplan et al. |
| 2010/0055438 A1 | 3/2010 | Kaplan et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0096763 A1 | 4/2010 | Kaplan et al. |
| 2010/0120116 A1 | 5/2010 | Kaplan et al. |
| 2010/0172952 A1* | 7/2010 | Srouji ............... A61L 27/46 424/423 |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2011/0009960 A1 | 1/2011 | Altman et al. |
| 2011/0046686 A1 | 2/2011 | Kaplan et al. |
| 2011/0076384 A1 | 3/2011 | Cannizzaro et al. |
| 2011/0135697 A1 | 6/2011 | Omenetto et al. |
| 2011/0152214 A1 | 6/2011 | Boison et al. |
| 2011/0167602 A1 | 7/2011 | Altman et al. |
| 2011/0171239 A1 | 7/2011 | Kaplan et al. |
| 2012/0121820 A1 | 5/2012 | Kaplan et al. |
| 2012/0123519 A1 | 5/2012 | Lovett et al. |
| 2012/0296352 A1 | 11/2012 | Altman et al. |
| 2013/0114917 A1 | 5/2013 | Sakamoto et al. |

FOREIGN PATENT DOCUMENTS

| | | |
|---|---|---|
| GB | 1182153 A | 2/1970 |
| JP | 55-139427 | 10/1980 |
| JP | 60-142259 A | 7/1985 |
| JP | 60-259677 | 12/1985 |
| JP | H01-118544 A | 5/1989 |
| JP | H05-43600 A | 2/1993 |
| JP | H06-346314 A | 12/1994 |
| JP | H08-295697 A | 11/1996 |
| JP | 10-36676 | 2/1998 |
| JP | H11-070160 A | 3/1999 |
| JP | 2000-273264 A | 10/2000 |
| JP | 2003-192807 A | 7/2003 |
| JP | 2004-068161 A | 3/2004 |
| JP | 2005-510268 A | 4/2005 |
| JP | 2006-504450 A | 2/2006 |
| JP | 2009-524507 A | 7/2009 |
| WO | WO-97/08315 A1 | 3/1997 |
| WO | WO-1999/001089 A1 | 1/1999 |
| WO | WO-2001/036531 | 5/2001 |
| WO | WO-011056626 A1 | 8/2001 |
| WO | WO-2002/072931 | 9/2002 |
| WO | WO-03/022909 A1 | 3/2003 |
| WO | WO-03/038033 A2 | 5/2003 |
| WO | WO-03/056297 A2 | 7/2003 |
| WO | WO-2004/000915 A2 | 12/2003 |
| WO | WO-04/041845 A2 | 5/2004 |
| WO | WO-2004/062697 A2 | 7/2004 |
| WO | WO-2005/000483 A1 | 1/2005 |
| WO | WO-2005/012606 A2 | 2/2005 |
| WO | WO-2005/123114 A2 | 12/2005 |
| WO | WO-2006/042287 A2 | 4/2006 |
| WO | WO-2006/076711 A2 | 7/2006 |
| WO | WO-2007/016524 A2 | 2/2007 |
| WO | WO-2008/106485 A2 | 9/2008 |
| WO | WO-2008/118133 A2 | 10/2008 |
| WO | WO-2008/118211 A2 | 10/2008 |
| WO | WO-2008/127401 A2 | 10/2008 |
| WO | WO-2008/127402 A2 | 10/2008 |
| WO | WO-2008/127404 A2 | 10/2008 |
| WO | WO-2008/127405 A2 | 10/2008 |
| WO | WO-2008/150861 A1 | 12/2008 |
| WO | WO-2009/023615 A1 | 2/2009 |
| WO | WO-2009/140588 A1 | 11/2009 |
| WO | WO-2010/042798 A2 | 4/2010 |
| WO | WO-2010/057142 A2 | 5/2010 |
| WO | WO 2010/141133 A2 * | 12/2010 ............. A61L 27/40 |
| WO | WO-2011/005381 A2 | 1/2011 |
| WO | WO-2011/006133 A2 | 1/2011 |
| WO | WO-2011/011347 A2 | 1/2011 |
| WO | WO 2011008842 A2 * | 1/2011 ........... A61L 15/225 |
| WO | WO-2011/041395 A2 | 4/2011 |

OTHER PUBLICATIONS

Altman, G.H. et al., Silk-based biomaterials, Biomaterials, 24:401-416 (2003).

Barrientos, S. et al., Growth factors and cytokines in wound healing, Wound Repair Regen., 16(5):585-601 (2008).

Chang, S.J. and Yang, S.S., Variability, related factors and normal reference value of post-void residual urine in healthy kindergarteners, J Urol., 182(4 Suppl):1933-8 (2009).

Demidova-Rice, T.N. et al., Acute and impaired wound healing: pathophysiology and current methods for drug delivery, part 2: role of growth factors in normal and pathological wound healing: therapeutic potential and methods of delivery, Adv. Skin Wound Care, 25(8):349-70 (2012).

Demura, M. and Asakura, T., Immobilization of glucose oxidase with Bombyx mori silk fibroin by only stretching treatment and its application to glucose sensor, Biotechnol. Bioeng., 33(5):598-603 (1989).

Extended European Search Report for EP 13746027.5, 18 pages (dated Jan. 4, 2016).

Freytes, D.O. et al., Hydrated versus lyophilized forms of porcine extracellular matrix derived from the urinary bladder, J. Biomed. Mater. Res. A., 87(4):862-72 (2008).

Gomez, P. 3rd. et al., The effect of manipulation of silk scaffold fabrication parameters on matrix performance in a murine model of bladder augmentation, Biomaterials, 32(30):7562-70 (2011).

Hofmann, S. et al., Control of in vitro tissue-engineered bone-like structures using human mesenchymal stem cells and porous silk scaffolds, Biomaterials, 28(6):1152-62 (2007).

Hu, X. et al., Regulation of Silk Material Structure by Temperature-Controlled Water Vapor Annealing, Biomacromolecules, 12:1686-1696 (2011).

International Search Report for PCT/US2013/024744, 5 pages (dated May 23, 2013).

Jin, I.J. et al., Water-Stable Silk Films with Reduced Beta-Sheet Content, Adv. Funct. Mater., 15:1241-1247 (2005).

Kim, U.-J. et al., Three dimensional aqueous-derived biomaterial scaffolds from silk fibroin, Biomaterials, 26(15):2775-85 (2005).

Kim, U., et al., Structure and Properties of Silk Hydrogels, Biomacromolecules, 5:786-792 (2004).

Kiwanuka, E. et al., Harnessing growth factors to influence wound healing, Clin. Plast. Surg., 39(3):239-48 (2012).

Kropp, B.P. et al., Experimental assessment of small intestinal submucosa as a bladder wall substitute, Urology, 46(3):396-400 (1995).

Li, M. et al., Study on Porous Silk Fibroin Materials. II. Preparation and Characteristics of Spongy Porous Silk Fibroin Materials, Journal of Applied Polymer Science, 79:2192-2199 (2001).

(56) References Cited

OTHER PUBLICATIONS

Lu, S. et al., Stabilization of Enzymes in Silk Films, Biomacromolecules, 10:1032-1042 (2009).
Lucas F. et al., The silk fibroins, Advances in Protein Chemistry, 13:107-242 (1958).
Matsumoto, A., et al., Mechanisms of Silk Fibroin Sol—Gel Transitions, J. Phys. Chem, B, 110:21630-21638 (2006).
Mauney, J.R. et al., Evaluation of gel spun silk-based biomaterials in a murine model of bladder augmentation, Biomaterials, 32(3):808-18 (2011).
Min, S. et al., Preparation and Characterization of Crosslinked Porous Silk Fibroin Gel, Sen'l Gakkaishi, 54(2):85-92 (1997).
Nazarov, R. et al., Porous 3-D scaffolds from regenerated silk fibroin, Biomacromolecules, 5(3):718-26 (2004).
Park, J.H. et al., the effect of heat on skin permeability, International Journal of Pharmacology, 359(1-2):94-103 (2008).
Peplow, P.V. and Baxter, G.D., Gene expression and release of growth factors during delayed wound healing: a review of studies in diabetic animals and possible combined laser phototherapy and growth factor treatment to enhance healing, Photomed. Laser Surg., 30(11):617-36 (2012).
Rockwood, D.N. et al., Materials Fabrication from *Bombyx mori* Silk Fibroin, Nature Protocols 6(10):1612-1631 (2011).
Sato, M. et al., Small-diameter vascular grafts of Bombyx mori silk fibroin prepared by a combination of electrospinning and sponge coating, Materials Letters, 64(16):1786-1788 (2010).
Supplementary Partial European Search Report for EP13746027, 8 pages (dated Sep. 7, 2015).
Wang, H. et al., A study on the flow stability of regenerated silk fibroin aqueous solution, International Journal of Biological Macromolecules, 36(1-2):66-70 (2005).
Wenk, et al., Silk Fibroin Spheres as a Platform for Controlled Drug Delivery, Journal of Controlled Release, 132(1):26-34 (2008).
Written Opinion for PCT/US2013/024744, 5 pages (dated May 23, 2013).
Wu, L. and Ding, J., In vitro degradation of three-dimensional porous poly(D,L-lactide-co-glycolide) scaffolds for tissue engineering, Biomaterials, (27):5821-30 (2004).
U.S. Appl. No. 14/249,138.
Agarwal, et al., Effect of Moisture Absorption on the Thermal Properties of Bombyx mori Silk Fibroin Films, Journal of Applied Polymer Science, 63(3):401-410 (1997).
Asakura, T. et al., Conformational characterization of Bombyx mori silk fibroin in the solid state by high-frequency carbon-13 cross polarization-magic angle spinning NMR, x-ray diffraction, and infrared spectroscopy, Macromolecules, 18(10):1841-1845 (1985).
Asakura, T. et al., NMR of silk fibroin 2. 13C NMR study of the chain dynamics and solution structure of Bombyx mori silk fibroin, Macromolecules, 17:1075-1081 (1984).
Chen et al., pH sensitivity and ion sensitivity of hydrogels based on complex-forming chitosan/silk fibroin interpenetrating polymer network, J. Appl. Polymer Sci., 65:2257-62 (1997).
Chen et al., Separation of alcohol-water mixture by pervaporation through a novel natural polymer blend membrane-chitosan/silk fibroin blend membrane, J. Appl. Polymer Sci., 73:975-980 (1999).
Chen, X. et al., Conformation transition kinetics of Bombyx mori silk protein, Proteins: Structure, Function, and Bioinformatics, 68:223-231 (2007).
Database WPI Week 198205, Derwent Publications Ltd., London, GB; AN 1982-09092E & JP 56 166235 A, Abstract (Dec. 21, 1981).
Demura, M. and Asakura, T., Porous membrane of Bombyx mori silk fibroin: structure characterization, physical properties and application to glucose oxidase immobilization, J. Membrane Science, 59:39-52 (1991).
Demura, M. et al., Immobilization of Biocatalysts with Bombyx mori Silk Fibroin by Several Kinds of Physical Treatment and its Application to Glucose Sensors, Biosensors, 4(6):361-372 (1989).
Derwent Record, Production of aqueous solution of silk fibroin at high concentration, Abstract of JP 08295697 A2, Nov. 12, 1996.
Doshi et al., Electrospinning Process and Applications of Electrospun Fibers, J/ Electrostatics, 35:151-160 (1995).
Freddi et al., Silk fibroin/cellulose blend films: preparation, structure, and physical properties, J Appl Polymer Sci, 56:1537-1545 (1995).
Fridrikh, S.V. et al., Controlling the fiber diameter during electrospinning, Phys. Rev. Lett., 90(14):144502 (2003).
Hijirida et al., 13C NMR of Nephila clavipes Marjo Ampullate Silk Gland, Biophysical Journal 71:3442-3447 (1996).
Hinman, M.B. et al., Synthetic spider silk: a modular fiber, Trends Biotechnol, 18(9):374-9 (2000).
Hu, X. et al., Determining Beta-Sheet Crystallinity in Fibrous Proteins by Thermal Analysis and Infrared Spectroscopy, Macromolecules, 39:6161-6170 (2006).
Huang et al., Engineered collagen-PEO nanofibers and fabrics, J Biomater Sci Polymer Edn, 12(9):979-993 (2001).
Huang et al., Generation of Synthetic Elastin-Mimetic Small Diameter Fibers and Fiber Networks, Macromolecules, 33:2989-2997 (2000).
International Search Report for PCT/US2010/041953, 4 pages (dated Mar. 31, 2011).
Jin, H.J. et al., Electrospinning Bombyx mori silk with poly(ethylene oxide), Biomacromolecules, 3(6):1233-9 (2002).
Kowalewski et al., Experiments and modelling of electrospinning process, Bulletin of the Polish Academy of Sciences, 53(4):385-394 (2005).
Kweon et al., Preparation of Semi-Interpreting Polymer Networks Composed of Silk Fibroin and Poly( ethylene glycol) Macromer, J. Appl. Polymer Sci., 80:1848-1853 (2001).
Lawrence, et al., Processing methods to control silk fibroin film biomaterial features, J. Mater. Sci., 43:6967-6985 (2008).
Lazaris, A. et al., Spider silk fibers spun from soluble recombinant silk produced in mammalian cells, Science. 295(5554):472-6 (2002).
Liang, C. X., et al., Improvements of the physical properties of fibroin membranes with sodium alginate, J. Appl. Polymer Sci., 1937-1943 (1992).
Liu, Y. et al., Proline and processing of spider silks, Biomacromolecules, 9(1):116-21 (2008).
Megeed et al., Controlled Release of Plasmid DNA from a Genetically Engineered Silk-Elastin like Hydrogel, Pharmaceutical Research, 19(7):954-959 (2002).
Mi et al., Control of wound infections using a bilayer chitosan would dressing with sustainable antibiotic delivery, J. Biomed. Mat. Res., 59:438-439 (2002).
Mi, F.L. et al., Fabrication and characterization of a sponge-like asymmetric chitosan membrane as a wound dressing, Biomaterials, 22(2):165-73 (2001).
Petrini et al., Silk fibroin-polyurethane scaffolds for tissue engineering, Journal of Materials Science: Materials in Medicine, 12:849-853 (2001).
Reneker D.H. and Chun, I., Nanometre diameter fibres of polymer, produced by electrospinning, Nanotechnology, 7:216-223 (1996).
Reneker of al., Electrospinning jets and polymer nanofibers, Polymer, 49:2387-2425 (2008).
Sawyer et al., Dextran therapy in thrombophlebitis. Abstract, JAMA, 191(9):740-742 (1965).
Sugihara, A. et al., Promotive effects of a silk film on epidermal recovery from full-thickness skin wounds, Proc. Soc. Exp. Biol. Med., 225(1):58-64 (2000).
Tanaka, K. et al., Hydrophobic interaction of P25, containing Asn-linked oligosaccharide chains, with the H-L complex of silk fibroin produced by Bombyx mori, Insect Biochem. Mol. Biol., 29(3):269-76 (1999).
Van Der Heijden et al., Phase behavior of polymer-diluent systems characterized by temperature modulated differential scanning calorimetry, Thermochimica Acta, 378:27-34 (2001).
Vepari, C. et al., Silk as a Biomaterial, Prog. Polym. Sci., 32(8-9): 991-1007 (2007).
Wang et al., Mechanical properties of electrospun silk fibers, Macromolecules, 37:6856-6864 (2004).
Wang et al., Production of submicron diameter silk fibers under benign processing conditions by two-fluid electrospinning, Macromolecules, 39:1102-1107 (2006).

(56) References Cited

OTHER PUBLICATIONS

Wang, X. et al., Biomaterial Coatings by Stepwise Deposition of Silk Fibroin, Langmuir, 21(24):11335-11341 (2005).

Wong et al., Solution behavior of synthetic silk peptides and modified recombinant silk proteins, Appl. Phys. A-Mater, 82:193-203 (2006).

Written Opinion for PCT/US2010/041953, 6 pages (dated Mar. 31, 2011).

Yamada et al., AFM observation of silk fibroin on mica substrates: morphologies reflecting the secondary structure, Thin Solid Films, 440:208-16 (2003).

Zhou et al., Preparation of a novel core-shell nanostructured gold colloid-silk fibroin bioconjugate by the protein in situ redox technique at room temperature, Chem Commun, 2518-2519 (2001).

Zhou, C.Z. et al., Fine organization of Bombyx mori fibroin heavy chain gene, Nucleic Acids Res., 28(12):2413-9 (2000).

Algarrahi, et al., Acellular Bi-Layer Silk Fibroin Scaffolds Support Functional Tissue Regeneration in a Rat Model of ONlay Esophagoplasty. Biomaterials. 2015; 53:149-159.

Chung, et al., Acellular Bi-Layer Silk Fibroin Scaffolds Support Tissue Regeneration in a Rabbit Model of Onlay Urethroplasty. PLoS One. 2014; 9(3):e91592.

Kim, et al., A transparent artificial dura mater made of silk fibroin as an inhibitor of inflammation in craniotomized rats. J Neurosurg. 2011; 114:435-490.

Kundu, et al., Silk fibroin biomaterials for tissue regenerations. Advanced Drug Delivery Reviews. 2013; 65:457-470.

Seth, et al., The Performance of Silk Scaffolds in a Rat Model of Augmentation Cystoplasty. Biomaterials. 2013; 34(20):4758-4765.

\* cited by examiner

CYSTOGRAMS

1 MONTH AUGMENT  3 MONTH AUGMENT (ARROW DENOTES IMPLANT AREA)

URODYNAMICS

ANIMAL SIZE
PRE-OP:
45.2 kg
3 MONTH AUGMENT:
53 kg
NON SURGICAL
CONTROL:
52.3 kg

| GROUPS | UTS (MPa) | EM (MPa) | ETF (%) |
| --- | --- | --- | --- |
| SILK (GS1) | 0.42±0.06* | 2.7±0.35* | 28±3* |
| SILK (GS2) | 0.54±0.09* | 2.7±0.6* | 51±6* |
| SILK (FF) | 0.29±.04 | 1.7±0.16 | 197±45 |
| SIS | 17.1±3.8 | 5.8±0.33 | 48±4 |

| GROUPS | STONE FREQUENCY | STONE DIAMETER (mm) |
|---|---|---|
| CYSTOTOMY | 1/8 (13%) | 2 |
| SIS | 4/7 (57%) | 4±2 |
| SILK (GS1) | 6/8 (75%) | 4±1 |
| SILK (GS2) | 5/7 (71%) | 3±3 |
| SILK (FF) | 2/10 (20%) | 2±1 |

| URODYNAMIC PARAMETERS | CYSTOTOMY | SIS | SILK (GS1) | SILK (GS2) | SILK (FF) |
|---|---|---|---|---|---|
| VOIDED VOLUME (ml) | 0.44±0.07 | 0.79±0.17 | 1.51±0.18* | 1.13±0.25 | 0.86±0.06* |
| INTERCONTRACTION INTERVAL (min) | 4.44±0.90 | 8.68±2.18 | 16.70±2.00* | 12.05±2.67 | 7.78±0.77* |
| COMPLIANCE (ml/cm H2O) | 8.37±2.09 | 12.59±3.08 | 20.56±5.01 | 11.26±1.83 | 82.31±9.98* |
| SNVC | 0.13±0.08 | 2.29±1.29* | 5.11±1.13* | 1.27±0.49* | 0.10±0.06 |
| PEAK VOIDING PRESSURE (cm H2O) | 41.46±5.03 | 51.40±9.25 | 42.04±3.39 | 53.21±4.87 | 36.52±4.42 |

*FIG. 7B*

STRUCTURAL ANALYSIS OF BI-LAYER
SILK SCAFFOLD AND PORCINE
BLADDER INTEGRATION

STRUCTURAL ANALYSIS OF BI-LAYER
SILK SCAFFOLD AND PORCINE
BLADDER INTEGRATION

STRUCTURAL ANALYSIS OF BI-LAYER
SILK SCAFFOLD AND PORCINE
BLADDER INTEGRATION

STRUCTURAL ANALYSIS OF BI-LAYER
SILK SCAFFOLD AND PORCINE
BLADDER INTEGRATION

| GROUPS | STONE FREQUENCY | STONE DIAMETER (mm) |
|---|---|---|
| CYSTOTOMY | 1/8 (13%) | 2 |
| SIS | 4/7 (57%) | 4±2 |
| SILK (GS1) | 6/8 (75%) | 4±1 |
| SILK (GS2) | 5/7 (71%) | 3±3 |
| SILK (FF) | 2/10 (20%) | 2±1 |

| URODYNAMIC PARAMETERS | CYSTOTOMY | SIS | SILK (GS1) | SILK (GS2) | SILK (FF) |
|---|---|---|---|---|---|
| VOIDED VOLUME (ml) | 0.44±0.07 | 0.79±0.17* | 1.51±0.18* | 1.13±0.25* | 0.86±0.06* |
| INTERCONTRACTION INTERVAL (min) | 4.44±0.90 | 8.68±2.18 | 16.70±2.00* | 12.05±2.67 | 7.78±0.77* |
| COMPLIANCE (ml/cm H2O) | 8.37±2.09 | 12.59±3.08 | 20.56±5.01 | 11.26±1.83 | 82.31±9.98* |
| SNVC | 0.13±0.08 | 2.29±1.29* | 5.11±1.13* | 1.27±0.49* | 0.10±0.06 |
| PEAK VOIDING PRESSURE (cm H2O) | 41.46±5.03 | 51.40±9.25 | 42.04±3.39 | 53.21±4.87 | 36.52±4.42 |

FIG. 11B

ONLAY URETHROPLASTY WITH SILK IMPLANT

RETROGRADE URETHROGRAMS AT 3 MONTHS POST-OP

MULTI-LAYER BIOMATERIAL FOR TISSUE REGENERATION AND WOUND HEALING

CROSS-REFERENCE TO RELATED APPLICATIONS

This application is the National Stage of International Application No. PCT/US2013/024744, filed Feb. 5, 2013, which claims benefit under 35 U.S.C. § 119(e) of U.S. Provisional Application No. 61/595,233 filed Feb. 6, 2012, the contents of both of which are incorporated herein by reference in their entirety.

GOVERNMENT SUPPORT

This invention was made with government support under grant numbers DK083616, DK065298 and EB002520 awarded by the National Institutes of Health. The government has certain rights in the invention.

TECHNICAL FIELD

The technology described herein relates to biomaterial compositions and methods of making and using them.

BACKGROUND

A number of biomaterials, including acellular matrices, tissue grafts, and polymeric substances (e.g. PGA) have been explored for use in tissue regeneration and/or wound healing. However, existing scaffolds, while permitting a certain level of tissue regeneration lead to long-term graft failure due to implant contracture, graft rupture, and/or fibrosis. These problems lead to delays in wound healing and even morbidity.

SUMMARY

The technology described herein is directed to multi-layer biomaterial compositions and methods relating thereto. The layers of these compositions differ in their physical properties and provide a complete composition that serves both as a scaffold for tissue regeneration as well as a suturable substrate capable of sealing a wound or tissue defect.

In one aspect, the technology described herein relates to a composition comprising a first and second layer; the first layer comprising a porous biomaterial matrix; and the second layer comprising an impermeable biomaterial. In some embodiments, the matrix can be a structure selected from the group consisting of: foams; hydrogels; electrospun fibers; gels; fiber mats; sponges; 3-dimensional scaffolds; non-woven mats; woven materials; knit materials; fiber bundles; and fibers. In some embodiments, the biomaterial can be selected from the group consisting of silk fibroin; PGA; collagen; polyethylene oxide, collagen, fibronectin, keratin, polyaspartic acid, polylysin, alginate, chitosan, chitin, and hyaluronic acid. In some embodiments, the silk fibroin can comprise *Bombyx mori* silk fibroin. In some embodiments, the first and second layers can comprise the same biomaterial. In some embodiments, the first and second layers can comprise different biomaterials. In one aspect, described herein is a composition comprising a first and second layer; the first layer comprising a porous silk fibroin matrix; and the second layer comprising a impermeable silk fibroin film. In some embodiments, the composition can further comprise an agent. In some embodiments, agent can be selected from the group consisting of: an antibiotic; an agent to attract cells; a cell; a stem cell; a ligand; a growth factor; a platelet; and a component of extracellular matrix.

In some embodiments, the average pore size of the biomaterial matrix can be at least 200 µm. In some embodiments, the average pore size of the biomaterial matrix can be at least 300 µm. In some embodiments, the average pore size of the biomaterial matrix can be at least 400 µm. In some embodiments, the average pore size of the biomaterial matrix can be from about 200 µm to about 600 µm. In some embodiments, the average pore size of the biomaterial matrix can be from about 300 µm to about 500 µm. In some embodiments, the average pore size of the biomaterial matrix can be about 400 µm. In some embodiments, the average pore size of the biomaterial matrix can be about 300 µm.

In some embodiments, the impermeable layer can be from about 10 µm to about 600 µm thick. In some embodiments, the impermeable layer can be from about 100 µm to about 400 µm thick. In some embodiments, the impermeable layer can be from about 150 µm to about 250 µm thick. In some embodiments, the impermeable layer can be from about 25 µm to about 150 µm thick. In some embodiments, the impermeable layer can be about 200 µm thick. In some embodiments, the composition can be from about 0.01 cm to about 5 cm thick. In some embodiments, the composition can be from about 0.1 cm to about 3 cm thick. In some embodiments, the composition can be from about 0.1 cm to about 2 cm thick. In some embodiments, the composition can be about 1 cm thick.

In some embodiments, the composition can have a shape selected from the group consisting of: a sheet; a tube; and a contoured sheet.

In one aspect, the technology described herein relates to a method of producing a composition as described herein, the method comprising; contacting a porous biomaterial matrix with a impermeable biomaterial layer. In one aspect, the technology described herein relates to a method of producing a composition as described herein, the method comprising; (a) casting an admixture of aqueous biomaterial solution and NaCl; (b) contacting the composition resulting from step (a) with water. In some embodiments, step (a) can be performed with the solution in contact with a pre-existing impermeable biomaterial layer. In some embodiments, the NaCl can be granular.

In some embodiments, the biomaterial solution can be a silk fibroin solution. In some embodiments, the silk fibroin solution can have a concentration of from about 2% wt/vol to about 15% wt/vol. In some embodiments, the silk fibroin solution can have a concentration of from about 4% wt/vol to about 10% wt/vol. In some embodiments, the silk fibroin solution can have a concentration of about 6% wt/vol.

In some embodiments, the admixture can be cast for from about 12 hours to about 96 hours. In some embodiments, the admixture can be cast for from about 24 hours to 72 hours. In some embodiments, the admixture can be cast for about 48 hours. In some embodiments, step (b) can proceed for from about 12 hours to about 120 hours. In some embodiments, step (b) can proceed for from about 24 hours to about 96 hours. In some embodiments, step (b) can proceed for about 72 hours.

In some embodiments, the water can be distilled water. In some embodiments, the water can be removed and replaced with a fresh volume of water at least once during step (b). In some embodiments, during the casting step, the admixture of biomaterial solution and NaCl can be in contact with an impermeable layer. In some embodiments, the impermeable biomaterial layer can comprise silk fibroin.

In some embodiments, the method can further comprises a first step of casting silk fibroin solution to form an impermeable silk fibroin layer. In some embodiments, the silk fibroin solution can have a concentration of from about 2% wt/vol to about 15% wt/vol. In some embodiments, the silk fibroin solution can have a concentration of from about 4% wt/vol to about 10% wt/vol. In some embodiments, the silk fibroin solution can have a concentration of about 8% wt/vol.

In some embodiments, the composition can be produced under sterile conditions or sterilized after the rinsing step is complete. In some embodiments, the composition can be produced in a linear shape. In some embodiments, the composition can be produced in a tubular shape. In some embodiments, the method can further comprise adding an agent to at least one layer. In some embodiments, the agent can be a therapeutic agent. In some embodiments, the method can further comprise altering the β-sheet content of a silk fibroin layer. In some embodiments, the β-sheet content of a silk fibroin layer can be altered using a method selected from the group consisting of: contacting the layer with water vapor; drying; dehydration; water annealing; stretching; compression; solvent immersion; immersion in methanol; immersion in ethanol; pH adjustment; heat treatment; and sonication. In some embodiments, the β-sheet content of a silk fibroin layer can be altered after adding an agent to the layer.

In one aspect, the technology described herein relates to a method for wound healing or repair of a tissue defect, the method comprising applying a composition as described herein to the wound or tissue defect. In some embodiments, the wound or tissue defect can be located in a hollow organ. In some embodiments, the hollow organ can be selected from the group consisting of: the bladder; a portion of the gastrointestinal tract; the stomach, and the intestines. In some embodiments, the wound or tissue defect can be selected from the group consisting of: a skin wound or defect; a diabetic ulcer; a bone wound or defect; a joint wound or defect; a meniscus wound or defect; an articular cartilage wound or defect; a soft tissue wound or defect; a lung tissue wound or defect; and a kidney wound or defect. In some embodiments, the impermeable layer can be oriented to prevent the movement of material into or out of the wound or defect.

BRIEF DESCRIPTION OF THE DRAWINGS

FIG. 5A depicts photomicrographs of representative SEM images demonstrating top and cross-sectional views of matrix configurations. Inset: Bottom FF scaffold view.

FIG. 5B depicts the results of evaluation of ultimate tensile strength (UTS), elastic modulus (EM), and % elongation to failure (ETF) in matrix groups defined in FIG. 5A. Means±standard deviation per data point. (*) represents data previously reported in Gomez et al., 2011.

FIG. 6A is a table of the quantification of stone frequency and diameter in bladders augmented with each matrix group and cystotomy controls. FIG. 6B depicts photomicrographs of urinary stones in regenerated bladders and controls. Arrows denote stones. Scale bar=2.5 mm.

FIGS. 7A-7B depict cystometric analysis and quantification of urodynamic parameters in augmented bladders following 10 weeks post-implantation. FIG. 7A depicts representative cystometric tracings of voiding cycles displayed by cystotomy controls, GS1, GS2, and FF augmented bladders. (*) denotes individual voids. FIG. 7B depicts a table of comparisons of urodynamic parameters between experimental groups displayed in [A]. (*)=p<0.05 in comparison to cystotomy controls.

FIGS. 8A (pre-op) and 8B (3 month post-implant) depict cystograms of bladders. FIG. 8C depicts cystometric analysis of bladder capacity (capacity at 20 cm H2O) pre-op and 3 months after augmentation with silk scaffold.

FIGS. 9A (side view) and 9B (top view) depict images of electron microscopy of a bi-layer scaffold. FIG. 9C depicts an image of a bi-layer scaffold composition. FIG. 9D depicts a view of bladder dome with implanted scaffold.

FIG. 10A depicts a table of stone frequency and diameter in each treatment group. FIG. 10B depicts photographs of stone formation.

FIGS. 11A-11B depict representative cystometric tracings of voiding cycles displayed by experimental groups (FIG. 11A) and comparisons of urodynamic parameters (FIG. 11B) of the tracings shown in FIG. 11B. (*)=p<0.05 in comparison to cystotomy FIG. 12A depicts stress-strain profiles of regenerated and control tissues. FIG. 12B depicts contraction responses in intact (+M) and demucosalized smooth muscle (−M) in reponse to carbachol in organ bath cultures. Dome-regenerated tissue. Body-normal bladder. Molar concentrations of carbachol are shown on the x-axis.

FIG. 19A depicts an image of the model of surgical procedure and silk implantation within rabbit urethra. FIG. 19B depicts retrograph urethrograms demonstrating no reduction in urethral caliber or stricture formation following 3 months of silk implantation. Controls represent urethras which were surgically incised, claosed, and maintained in parallel with silk implanted animals. Results are representative of N=2 animals performed with silk implants as well as controls. Arrows denote original implantation site or sham injury.

DETAILED DESCRIPTION

Figure 1:
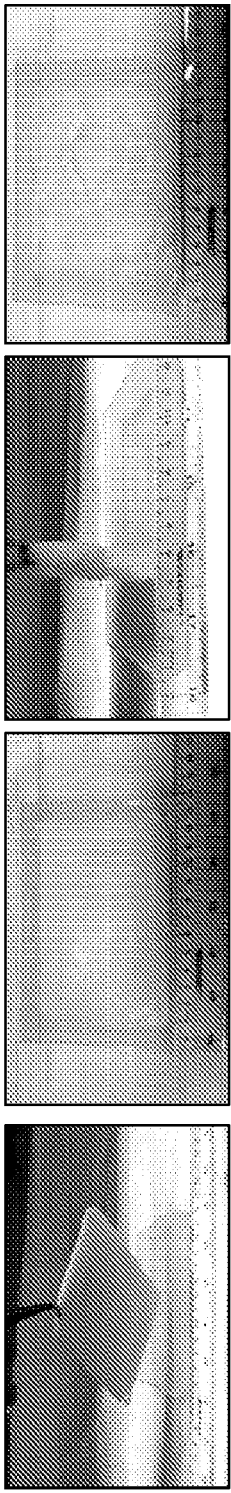
FIG. 1 depicts scanning electron microscopy analysis and tensile testing of the structural and mechanical properties of bilayer compositions produced according to Method 1 of Example 1.

Described herein are compositions relating to a multi-layer biomaterial composition and methods relating thereto. As described herein, the inventors have demonstrated that multi-layer biomaterial compositions comprising at least a porous biomaterial matrix layer and an impermeable biomaterial layer provide a scaffold for tissue regeneration, elasticity properties that mimic native tissues, a readily suturable substrate, and the ability to effectively seal a wound or defect (e.g. prevent the passage of fluids and/or cellular materials through the wound or defect). As further demonstrated, these multilayer compositions provide improvements in wound healing as compared to monolayer compositions.

In one aspect, described herein is a composition comprising a first and second layer; the first layer comprising a porous biomaterial matrix; and the second layer comprising an impermeable biomaterial.

As used herein, the term "matrix" refers to the physical structure which contains the biomaterial. Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats (See, e.g. Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g. electrospun matrices can have greater surface area than foams and can thus be preferable in applications where, e.g. lung and/or kidney tissue is to be regenerated, as the greater surface area encourages mass/gas exchange.

In some embodiments, the composition is a hydrogel. As used herein, the term "hydrogel" refers to a three-dimensional polymeric structure that is insoluble in water but which is capable of absorbing and retaining large quantities of water to form a stable, often soft and pliable, structure. In some embodiments, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are super-absorbent (they can contain over 99% water) and can be comprised of natural (e.g., silk) or synthetic polymers, e.g., PEG.

In some embodiments, the impermeable layer can be in the form of a film. Thickness of the film can range from nanometers to millimeters. For example, film thickness can range from about 1 nm to about 1000 mm. In some embodiments, the film thickness can be from about 1 nm to 1000 nm, from about 1 µm about 1000 µm, from about 1 mm to about 1000 mm. In some embodiments, the film thickness can be from about 500 nm to about 750 µm, from about 750 nm to about 500 µm, from about 1000 nm to about 250 µm, from about 10 µm to about 100 µm, from about 25 µm to about 75 µm. In some embodiments, film thickness ranges from about 10 nm to about 1 mm.

In some embodiments, the porous matrix layer can be in the form of a foam. Foams can be made from methods known in the art, including, for example, freeze-drying and gas foaming in which water is the solvent or nitrogen or other gas is the blowing agent, respectively, or by, e.g. leaching with salt and/or water-soluble particles.

The biomaterial matrix of the first layer is a porous biomaterial matrix. i.e., the matrix has porosity. As used herein, the term "porosity" means the fractional volume (dimension-less) of the composition that is composed of open space, e.g., pores or other openings. Thus, porosity measures void spaces in a material and is a fraction of volume of voids over the total volume, as a percentage between 0 and 100% (or between 0 and 1). See for example, Coulson J. M., et. al., Chemical Engineering, 1978, volume 2, $3^{rd}$ Edition, Pergamon Press, 1978, page 126). Determination of matrix porosity is well known to a skilled artisan, e.g., using standardized techniques, such as mercury porosimetry and gas adsorption, e.g., nitrogen adsorption. Generally, porosity of the composition can range from 0.5 to 0.99, from about 0.75 to about 0.99, or from about 0.8 to about 0.95. In some embodiments, porosity of the composition can be at least 0.75. In some embodiments, porosity of the composition can be at least 0.8. In some embodiments, porosity of the composition can be at least 0.9.

The porous layer provides for, e.g. cell migration and tissue regeneration. The pore size of the pourous layer can vary, e.g. accordingly to the size and/or shape of the cells and/or tissue which will be regenerated. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. In some embodiments, a hydrogel can be swollen when the hydrogel is hydrated. The sizes of the pores size can then change depending on the water content in the hydrogel. The pores can be filled with a fluid such as water or air. It will be understood by one of ordinary skill in the art that pores can exhibit a distribution of sizes around the indicated "size." Unless otherwise stated, the term "size" as used herein refers to the mode of a size distribution of pores, i.e., the value that occurs most frequently in the size distribution.

The pores can be substantially round cross-section or opening. What is meant by "substantially round" is that the ratio of the lengths of the longest to the shortest perpendicular axes of the pore cross-section is less than or equal to about 1.5. Substantially round does not require a line of symmetry. In some embodiments, the ratio of lengths between the longest and shortest axes of the pore cross-section is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1.

Figure 16:
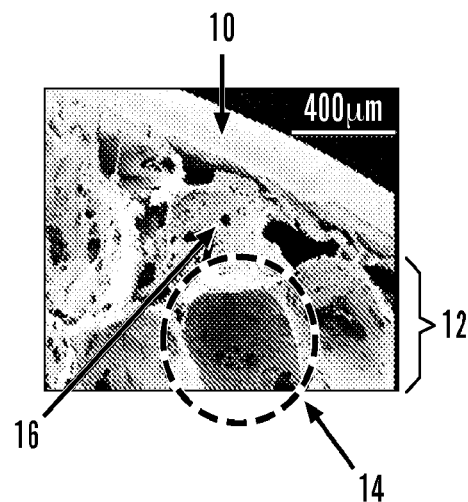
FIG. 16 depicts an electromicrography demonstrating the presence of primary and secondary pores in a porous layer.

In some embodiments, the average pore size of the biomaterial matrix can be at least 200 µm. In some embodiments, the average pore size of the biomaterial matrix can be at least 300 µm. In some embodiments, the average pore size of the biomaterial matrix can be at least 400 µm. In some embodiments, the average pore size of the biomaterial matrix can be from about 200 µm to about 600 µm. In some embodiments, the average pore size of the biomaterial matrix can be from about 300 µm to about 500 µm. In some embodiments, the average pore size of the biomaterial matrix can be about 400 µm. In some embodiments, the average pore size of the biomaterial matrix can be about 300 µm. The average pore size of the matrix can be the average size (e.g. diameter) of all the pores in the matrix. In some embodiments, the average pore size of the matrix can be the average pore size (e.g. diameter) of all the primary pores in the matrix. In some embodiments, the matrix can comprise primary and secondary pores (see, e.g. FIG. 16; where a single primary pore 14 is contained within the dashed line circle and a secondary pore 16 is indicated). The primary pores are substantially larger in diameter than the secondary pores and the secondary pores interconnected the primary pores. In some embodiments, the primary pores are the population of pores which have an average diameter at least 3× the average pore size of the remaining pores.

The second layer of the composition comprises an impermeable biomaterial layer. As used herein, "impermeable" refers to material being able to prevent the passage of an aqueous solution across the material at a particular temperature, tension and fluid pressure. In some embodiments, the impermeable layer can have no observable pores. In some embodiments, the impermeable layer can have no observable pores which transit the entire thickness of the layer.

The compositions described herein can be elastic. For example, the composition can have an extensibility of about 500%, about 400%, 300%, 200%, 100%, 50%, or about 25%. In some embodiments, the composition can have an elastic modulus in the range about 10-2 kPa to about 103 kPa. As used herein, the term "elastic modulus" refers to an object or substance's tendency to be deformed elastically (i.e., non-permanently) when a force is applied to it. Generally, the elastic modulus of an object is defined as the slope of its stress-strain curve in the elastic deformation region. Specifying how stress and strain are to be measured, including directions, allows for many types of elastic moduli to be defined. Young's modulus (E) describes tensile elasticity, or the tendency of an object to deform along an axis when opposing forces are applied along that axis; it is defined as the ratio of tensile stress to tensile strain. It is often referred to simply as the elastic modulus. The bulk modulus (K) describes volumetric elasticity, or the tendency of an object to deform in all directions when uniformly loaded in all directions; it is defined as volumetric stress over volumetric strain, and is the inverse of compressibility. The bulk modulus is an extension of Young's modulus to three dimensions. Three other elastic moduli are Poisson's ratio, Lame's first parameter, and P-wave modulus. In some embodiments, the composition can have an elastic modulus in the range from about 1 kPa to about 25 kPa. In some embodiments, the composition can have an elastic module of about 5 kPa, about 10 kPa, about 15 kPa, or about 20 kPa. In some embodiments, the composition can have an Young's modulus in the range of from about 15 kPa to about 35 kPa.

The first and second layers are arranged such that the second layer coats and/or covers no more than 70% of the surface area of the first layer, e.g. 70% or less, 60% or less, 50% or less, 40% or less, or 30% or less of the surface area of the first layer. In some embodiments, wherein the entire composition has a shape approximating a cuboid, the first layer can coat and/or cover one face of the cuboid. In some embodiments, wherein the entire composition has a shape approximating a cuboid, the first layer can coat and/or cover the entirety of one face of the cuboid. In some embodiments, where the entire composition has a shape approximating a sheet or plane, the first layer can coat and/or cover one face of the sheet or plane. In some embodiments, where the entire composition has a shape approximating a sheet or plane, the first layer can coat and/or cover the entirety of one face of the sheet or plane.

Each of the layers of the composition can comprise one or more biomaterials. As used herein, "biomaterial" refers to a material that is biocompatible and biodegradable. As used herein, the term "biocompatible" refers to substances that are not toxic to cells. In some embodiments, a substance is considered to be "biocompatible" if its addition to cells in vitro results in less than or equal to approximately 20% cell death. In some embodiments, a substance is considered to be "biocompatible" if its addition to cells in vivo does not induce inflammation and/or other adverse effects in vivo. As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

Non-limiting examples of biomaterials include, silk fibroin; PGA; collagen; fibronectin, keratin, polyaspartic acid, polylysin, alginate, chitosan, chitin, hyaluronic acid, glycosaminoglycan, silk, fibrin, MATRIGEL®, alginic acid, pectinic acid, carboxy methyl cellulose, hyaluronic acid, heparin, heparin sulfate, carboxymethyl chitosan, pullulan, gellan, xanthan, gelatin, carboxymethyl starch, carboxymethyl dextran, chondroitin sulfate, cationic guar, cationic starch, esters of alginic, or pectinic and the like. In some embodiments, a layer of the composition can comprise one or more biomaterials, e.g. one biomaterial, two biomaterials, three biomaterials, four biomaterials, or more biomaterials. In some embodiments, the first and second layer can comprise the same biomaterial and/or the same combination of biomaterials. In some embodiments, the first and second layer can comprise different biomaterials and/or different combinations of biomaterials.

In some embodiments, either layer can comprise silk fibroin. In some embodiments, both layers can comprise silk fibroin. In some embodiments, either layer can consist of silk fibroin. In some embodiments, both layers can consist of silk fibroin. In some embodiments, the silk fibroin comprises *Bombyx mori* silk fibroin. As used herein, the term "silk fibroin" includes silkworm fibroin and insect or spider silk protein. See e.g., Lucas et al., 13 Adv. Protein Chem. 107 (1958). Any type of silk fibroin can be used. Silk fibroin produced by silkworms, such as *Bombyx mori*, is the most common and represents an earth-friendly, renewable resource. For instance, silk fibroin can be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that can be used. An aqueous silk fibroin solution can be prepared using techniques known in the art. Suitable processes for preparing silk fibroin solution are disclosed, for example, in U.S. patent application Ser. No. 11/247,358; WO/2005/012606; and WO/2008/127401. The silk fibroin solution can be diluted to a lower concentration with deionized water, or can be concentrated, for example, to about 30% (w/v), if desired. Additionally, silk fibroin can be chemically modified with active agents in the solution, for example through diazonium or carbodiimide coupling reactions, avidin-biodin interaction, or gene modification and the like, to alter the physical properties and functionalities of the silk protein. See, e.g., PCT/US09/64673; PCT/US10/41615; PCT/US10/42502; U.S. application Ser. No. 12/192,588. In some embodiments, silk fibroin used herein can be depleted of sericin by any methods known in the art.

Alternatively, the silk fibroin solution can be produced using organic solvents. Such methods have been described, for example, in Li, M., et al., *J. Appl. Poly Sci.* 2001, 79, 2192-2199; Min, S., et al. *Sen'l Gakkaishi* 1997, 54, 85-92; Nazarov, R. et al., *Biomacromolecules* 2004 May-June; 5(3):718-26.

Various methods of producing silk matrix are known in the art. In some embodiments, a silk hydrogel can be produced by sonicating a silk solution containing silk or silk fibroin. See, e.g., U.S. Pat. App. No. U.S. 2010/0178304 and International App. No.: WO 2008/150861, the contents of which are incorporated herein by reference in their entirety for methods of silk fibroin gelation using sonication.

In alternative embodiments, the silk matrix can be produced by applying a shear stress to a silk solution. See, e.g., International App. No.: WO 2011/005381, the content of which is incorporated herein by reference in its entirety for methods of producing vortex-induced silk fibroin gelation for encapsulation and delivery.

In other embodiments, the silk hydrogel can be produced by modulating the pH of a silk solution. The pH of the silk solution can be altered by subjecting the silk solution to an electric field and/or reducing the pH of the silk solution with an acid. See, e.g., U.S. App. No.: US 2011/0171239, the content of which is incorporated herein by reference in its entirety, for details on methods of producing pH-induced silk gels.

Either and/or both layers of the compositions described herein can further comprise microparticles and/or nanoparticles, e.g. biomaterial microparticles and/or nanoparticles, optionally comprising a therapeutic agent. By way of non-limiting example, various methods of producing silk microparticles or nanoparticles are known in the art. In some embodiments, the silk microparticles or nanoparticles can be produced by a polyvinyl alcohol (PVA) phase separation method as described in, e.g., International App. No. WO 2011/041395, the content of which is incorporated herein by reference in their entirety for methods of silk fibroin gelation using sonication. Other methods for producing silk microparticles or nanoparticles, e.g., described in U.S. App. No. U.S. 2010/0028451 and International App. No.: WO 2008/118133 (using lipid as a template for making silk microspheres or nanospheres), and in Wenk et al. J Control Release 2008; 132: 26-34 (using spraying method to produce silk microspheres or nanospheres) can be used for the purpose of making silk microparticles or nanoparticles encapsulating a therapeutic agent. In some embodiments, the silk microparticles or nanoparticles can be further embedded in a biopolymer, e.g., to prolong the release of a therapeutic agent over a period of time. In some embodiments, the biopolymer can be a silk hydrogel to encapsulate the therapeutic agent-loaded silk microparticles or nanoparticles. See, e.g., International App. No.: WO 2010/141133 for methods of producing silk fibroin scaffolds for antibiotic delivery.

The layers of the present composition can further comprise at least one agent, e.g. 1 agent, 2 agents, 3 agents, 4 agents, 5 agents, or more agents. As used herein, an "agent" refers to any molecule or combination of molecules added to a composition during construction which is either a) not present in the biomaterial used to construct the composition. In some embodiments, the agent can be a bioactive agent or bioactive material. As used herein, "bioactive agents" or "bioactive materials" refer to naturally occurring biological materials, for example, extracellular matrix materials such as fibronectin, vitronection, and laminin; cytokins; and growth factors and differentiation factors. "Bioactive agents" also refer to artificially synthesized materials, molecules or compounds that have a biological effect on a biological cell, tissue or organ. The molecular weights of the bioactive agent can vary from very low (e.g. small molecules, 200-500 Daltons) to very high (e.g. plasmid DNA, ~2,000,000 Daltons). In some embodiments, the bioactive agent is a small molecule. As used herein, the term "small molecule" can refer to compounds that are "natural product-like," however, the term "small molecule" is not limited to "natural product-like" compounds. Rather, a small molecule is typically characterized in that it contains several carbon—carbon bonds, and has a molecular weight of less than 5000 Daltons (5 kD). In some embodiments, a small molecule can have a molecular weight of less than 3 kD. In some embodiments, a small molecule can have a molecular weight of less than 2 kD. In some embodiments, a small molecule can have a molecular weight of less than 1 kD. In some embodiments, a small molecule can have a molecular weight of less than 700 D.

In some embodiments, bioactive agent is a therapeutic agent. As used herein, the term "therapeutic agent" refers to a substance used in the diagnosis, treatment, or prevention of a disease. Any therapeutic agent known to those of ordinary skill in the art to be of benefit in the diagnosis, treatment or prevention of a disease is contemplated as a therapeutic agent in the context of the present invention. Therapeutic agents include pharmaceutically active compounds, hormones, growth factors, enzymes, DNA, plasmid DNA, RNA, siRNA, viruses, proteins, lipids, pro-inflammatory molecules, antibodies, antibiotics, anti-inflammatory agents, anti-sense nucleotides and transforming nucleic acids or combinations thereof. Any of the therapeutic agents may be combined to the extent such combination is biologically compatible.

Exemplary therapeutic agents include, but are not limited to, those found in *Harrison's Principles of Internal Medicine*, 13th Edition, Eds. T. R. Harrison et al. McGraw-Hill N.Y., NY; Physicians' Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

Non-limiting examples of agents can include an antibiotic; an agent to attract cells; a cell; a stem cell; a ligand; a growth factor; a platelet; an antinflammatory; a component of extracellular matrix; enzymes, proteins, nucleic acids, antibodies, antibiotics, hemostatic agents and the like, as described herein. See, e.g., WO2004/062697 and WO2005/012606. The agent can represent any material capable of being embedded in the biomaterials. For example, the active agent can be a therapeutic agent, or a biological material, such as peptides, nucleic acids (e.g., DNA, RNA, siRNA), nucleic acid analogs, nucleotides, oligonucleotides, peptide nucleic acids (PNA), aptamers, antibodies or fragments or portions thereof (e.g., paratopes or complementarity-determining regions), antibody-like molecules, antigens or epitopes, hormones, hormone antagonists, growth factors or recombinant growth factors and fragments and variants thereof, cell attachment mediators (such as RGD), cytokines, small molecules, drugs, dyes, amino acids, vitamins, antioxidants, antifungals, antivirals, prodrugs, or combinations thereof. See, e.g., PCT/US09/44117; U.S. Patent Application Ser. No. 61/224,618). The active agent can also be a combination of any of the above-mentioned agents. A cell, e.g. a platelet, can be autologous to the subject or obtained from a donor.

Exemplary antibiotic agents include, but are not limited to, actinomycin; aminoglycosides (e.g., neomycin, gentamicin, tobramycin); β-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Optionally, the antibiotic agents can also be antimicrobial peptides such as defensins, magainin and nisin; or lytic bacteriophage. The antibiotic agents can also be the combinations of any of the agents listed above. See also PCT/US2010/026190.

In some embodiments, the bioactive agent can be a growth factor or a cytokine. Suitable growth factors and cytokines include, but are not limited, to stem cell factor (SCF), granulocyte-colony stimulating factor (G-CSF), granulocyte-macrophage stimulating factor (GM-CSF), stromal cell-derived factor-1, steel factor, VEGF, TGFβ, platelet derived growth factor (PDGF), angiopoeitins (Ang), epidermal growth factor (EGF), bFGF, HNF, NGF, bone morphogenic protein (BMP), fibroblast growth factor (FGF), hepatocye growth factor, insulin-like growth factor (IGF-1), interleukin (IL)-3, IL-1α, IL-1β, IL-6, IL-7, IL-8, IL-11, and IL-13, colony-stimulating factors, thrombopoietin, erythropoietin, fit3-ligand, and tumor necrosis factor α (TNFα). Other examples are described in Barrientos et al. Wound Repair Regen 2008 16:585-601; Peplow and Baxter Photomed Laser Surg 2012 30:617-36; Demidova-Rice et al. Adv Skin Wound Care 2012 25:349-370; Kiwanuka et al. Clin Plast Surg 2012 39:239-248; each of which is incorporated by reference herein in its entirety.

The composition can further comprise hemostatic agents since hemostatic agents typically act to stop bleeding and tissue sealant can bind to and close defects in the tissues. Combining the hemostatic agents into the biomaterial can therefore present desirable features during surgical repair to prevent or stop bleeding as well as promote tissue reconstruction. Exemplary hemostatic agents suitable for use herein include, but are not limited to, thrombin, fibrin, fibrinogen, gelatin, collagen, polysaccharide, cellulose, blood factors, and combinations thereof.

Additional materials can also be blended into the biomaterial. Such materials include, but are not limited to, polyaspartic acid, polylysine, alginate, polycaprolactone, polylactic acid, polyglycolic acid, polyhydroxyalkanoates, dextrans, polyanhydrides, PEO, PEG, glycerol (see PCT/US2009/060135), and other biocompatible polymers, see WO 2004/0000915.

The biomaterial can be modified if desired. One of skill in the art can select appropriate methods to modify biomaterials, e.g., depending on the side groups of the biomaterial, desired reactivity of the biomaterial and/or desired charge density on the biomaterial. In one embodiment, modification of a biomaterial can use the amino acid side chain chemistry, such as chemical modifications through covalent bonding, or modifications through charge-charge interaction. Exemplary chemical modification methods include, but are not limited to, carbodiimide coupling reaction (see, e.g. U.S. Patent Application. No. US 2007/0212730), diazonium coupling reaction (see, e.g., U.S. Patent Application No. US 2009/0232963), avidin-biotin interaction (see, e.g., International Application No.: WO 2011/011347) and pegylation with a chemically active or activated derivatives of the PEG polymer (see, e.g., International Application No. WO 2010/057142). As a further non-limiting example, biomaterials, e.g. silk fibroin can also be modified through gene modification to alter functionalities of the biomaterial (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic-inorganic composite. See WO 2006/076711. Additionally, the biomaterial can be combined with a chemical, such as glycerol, that, e.g., affects flexibility of the composition. See, e.g., WO 2010/042798, Modified Silk films Containing Glycerol.

In some embodiments, the biomaterial provides controlled release of the delivery of the embedded active agents (e.g., therapeutic agents or biological materials). Controlled release permits dosages to be administered over time, with controlled release kinetics. In some instances, delivery of the therapeutic agent or biological material is continuous to the site where treatment is needed, for example, over several weeks. Controlled release over time, for example, over several days or weeks, or longer, permits continuous delivery of the therapeutic agent or biological material to obtain preferred treatments. The controlled delivery vehicle is advantageous because it protects the therapeutic agent or biological material from degradation in vivo in body fluids and tissue, for example, by proteases. See, e.g., PCT/US09/44117. Controlled release of the agent from the biomaterial can be designed to occur over time, for example, for greater than about 12 hours or 24 hours, inclusive; greater than 1 month or 2 months or 5 months, inclusive. The time of release can be selected, for example, to occur over a time period of about 12 hours to 24 hours, or about 12 hours to 1 week. In another embodiment, release can occur for example on the order of about 1 month to 2 months, inclusive. The controlled release time can be selected based on the condition treated. For example, a particular release profile can be more effective where consistent release and high local dosage are desired.

In an alternative embodiment, the biomaterials can include plasmonic nanoparticles to form photothermal elements. Thermal therapy has been shown to aid in the delivery of various agents, see Park et al., Effect of Heat on Skin Permeability, 359 Intl. J. Pharm. 94 (2008). In one embodiment, short bursts of heat on very limited areas can be used to maximize permeability with minimal harmful effects on surrounding tissues. Thus, plasmonic particle-doped biomaterial can add specificity to thermal therapy by focusing light to locally generate heat only via the biomaterials. In some embodiments, the biomaterials can include photothermal agents such as gold nanoparticles.

When referring to the "thickness" of the composition described herein, reference is being made the distance from one surface of the compostion to a second surface of the composition as measured along the shortest line which will cross both layers (see, e.g. FIG. 14B). In some embodiments, the impermeable layer can be from about 10 μm to about 600 μm thick. In some embodiments, the impermeable layer can be from about 100 μm to about 400 μm thick. In some embodiments, the impermeable layer can be from about 150 μm to about 250 μm thick. In some embodiments, the impermeable layer can be from about 25 μm to about 150 μm thick. In some embodiments, the impermeable layer can be about 200 μm thick. In some embodiments, the composition can be from about 0.01 cm to about 5 cm thick. In some embodiments, the composition can be from about 0.1 cm to about 3 cm thick. In some embodiments, the composition can be from about 0.1 cm to about 2 cm thick. In some embodiments, the composition can be about 1 cm thick.

The compositions described herein can be formed in any desired shape and size. The shape of the composition can be, by way of non-limiting example, a sheet; a tube; and a contoured sheet. In some embodiments, the compositions can be formed in substantially flat sheets. In some embodiments, the compositions can be formed in countoured sheets, e.g. sheet which have at least one curve, arc, or angle. In some embodiments, the contour of the sheet can be such that it matches the desired contour of the tissue to be regenerated. In some embodiments, the composition can be formed in a tube or a portion of a tube, e.g. a sheet which is curved, along one dimension, at least 45 degrees, e.g. 45 degrees or more, 90 degrees or more, 180 degrees or more, 200 degrees or more, 240 degrees or more, 300 degrees or more, or 360 degrees or more.

In some embodiments, the impermeable layer can extend beyond the porous layer, e.g. if the porous layer forms a 2"×2" cube, the impermeable layer can form a 3"×3" sheet on one face of the cube. This can provide a more complete seal around the wound and/or tissue defect and/or provide a substrate for, e.g. suturing.

In one aspect, described herein is a method of producing a composition as described herein, the method comprising contacting a porous biomaterial matrix with an impermeable biomaterial layer. Protein-protein interactions between the two layers are often sufficient to maintain the contact between the two layers, particularly when the porous biomaterial matrix is formed while in contact with the impermeable layer. In further embodiments, the layers can be annealed using methods known in the art, e.g. water annealing or exposing the layers to a methanol to reduce water solubility (see, e.g. Hu et al. Biomacromolecules 2011 12:1686-1696; which is incorporated by reference herein in its entirety). In further embodiments, the layers can comprise agents which cause the layers to maintain contact, e.g. one layer can comprise an antibody and the other layer can comprise the ligand for that antibody.

In one aspect, described herein is a method of producing a composition as described herein, the method comprising; (a) casting an admixture of aqueous biomaterial solution and a salt or water-soluble particle; (b) contacting the composition resulting from step (a) with water. In some embodiments, the salt can be NaCl.

Casting can comprise the solidification and/or gelation of an aqueous biomaterial over time as it gradually dehydrates. Methods for casting biomaterials, e.g. silk fibroin, are known in the art and described herein. See, e.g. descriptions of the generation of hydrogels (WO2005/012606; PCT/US08/65076; PCT/US08/65076), ultrathin films (WO2007/016524), thick films, conformal coatings (WO2005/000483; WO2005/123114), microspheres (PCT/US2007/020789), 3D porous matrices (WO2004/062697), combinations of the films, microspheres and porous matrices (PCT/US09/44117), solid blocks (WO2003/056297), and fibers with diameters ranging from the nanoscale (WO2004/0000915) to several centimeters (U.S. Pat. No. 6,902,932) have been explored with implications in biomaterials and regenerative medicine (WO2006/042287; U.S. patent application Ser. No. 11/407,373; PCT/US08/55072). Each of the foregoing references is incorporated by reference herein in its entirety.

The thickness of a material produced by casting can be controlled, e.g. by altering the amount and concentration of the biomaterial solution and the rate of drying or by physical manipulation, e.g. cutting of the cast product. The shape and size of a cast biomaterial can be controlled by the selection of a casting vessel, e.g. the vessel can have substantially the shape and/or size and/or contour that it is desired that the cast material assume.

Figure 15A:
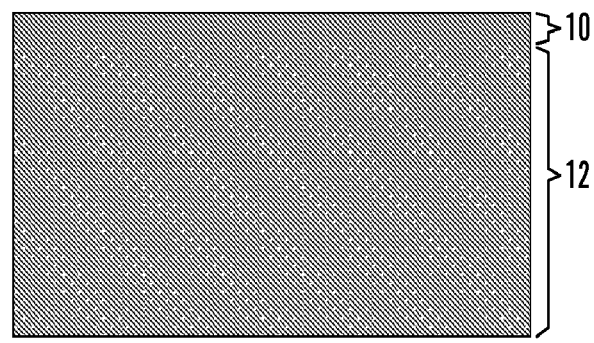
FIGS. 15A-15B depict schematics of exemplary embodiments of the compositions described herein.

In some embodiments, the impermeable layer forms spontaneously on the bottom of the composition. A schematic of an exemplary embodiment of such a composition is depicted in FIG. 15A, wherein the impermeable layer 10 is composed of the same biomaterial (at substantially the same concentration) as the porous matrix layer 12. In some embodiments, the spontaneously formed impermeable layer can be comprised, substantially, of the same biomaterial as the porous matrix. An exemplary embodiment of a protocol for producing such compositions is set forth in Example 9.

In some embodiments, step (a), as described above herein, can be performed with the solution in contact with a pre-existing impermeable biomaterial layer. The pre-existing impermeable layer can have been cast in the same casting mold, or cast in a different mold, and/or obtained by other methods (e.g. electrospinning). The pre-existing impermeable layer can be oriented in the casting mold in any desired configuration and/or location, e.g. in the bottom or on the side of the mold.

Figure 15B:
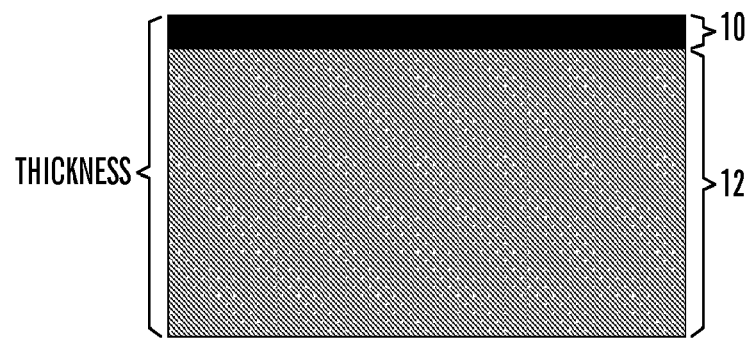

In some embodiments, the impermeable layer can comprise a different biomaterial, mix of biomaterials (and, e.g. agents), or different concentrations of biomaterial as the porous matrix layer. A schematic of an exemplary embodiment of such a composition is depicted in FIG. 15B, wherein the impermeable layer 10 is composed of a different biomaterial as the porous matrix layer 12.

In some embodiments, the impermeable biomaterial layer can comprise silk fibroin. In some embodiments, the method further can comprise a first step of casting silk fibroin solution to form an impermeable silk fibroin layer. In some embodiments, the silk fibroin solution can have a concentration of from about 2% wt/vol to about 15% wt/vol. In some embodiments, the silk fibroin solution can have a concentration of from about 4% wt/vol to about 10% wt/vol. In some embodiments, the silk fibroin solution can have a concentration of about 8% wt/vol. Films, e.g. silk fibroin films suitable for use as impermeable biolayers can be formed by casting of purified silk fibroin solution which crystallizes upon exposure to air, humidity or dry nitrogen gas, as some examples, without the need for exogenous crosslinking reactions or post processing crosslinking for stabilization. See, e.g., PCT/US07/83600; PCT/US07/83620: PCT/US07/83605: each of which is incorporated by reference herein in its entirety.

In some embodiments, the pores of the porous matrix are formed by the salt or water-soluble particle via salt-leaching. In some embodiments, the salt or water-soluble particle can be granular. In some embodiments, the salt or water-soluble particle can comprise crystals and/or grains having an average size of from about 300 μm to about 1000 μm. In some embodiments, the salt or water-soluble particle can comprise crystals and/or grains having an average size of from about 400 μm to about 800 μm. In some embodiments, the salt or water-soluble particle can comprise crystals and/or grains having an average size of from about 500 μm to about 600 μm.

In some embodiments, the biomaterial solution used to form the biomaterial matrix can be a silk fibroin solution. In some embodiments, the silk fibroin solution can have a concentration of from about 2% wt/vol to about 15% wt/vol. In some embodiments, the silk fibroin solution can have a concentration of from about 4% wt/vol to about 10% wt/vol. In some embodiments, the silk fibroin solution can have a concentration of about 6% wt/vol.

The admixture can be cast for until the desired thickness of the porous layer is produced. The necessary time will vary, as described elsewhere herein, and is readily determined and adjusted by one of ordinary skill in the art. In some embodiments, the admixture can be cast for from about 12 hours to about 96 hours. In some embodiments, the admixture can be cast for from about 24 hours to 72 hours. In some embodiments, the admixture can be cast for about 48 hours.

Step (b) of the methods described above herein removes the salt or water-soluble particle, leaving pores in the biomaterial matrix. Step (b) can proceed, e.g. until the salt or water-soluble particle has been substantially removed from the composition, e.g. until less than 10% of the salt or water-soluble particle remains and/or until 90% of the pores (e.g. primary pores) no longer contain detectable grains and/or crystals of salt or water-soluble particle. The amount of time necessary for step (b) can therefore vary according with the thickness of the composition, the volume of water used, the temperature of the water, and/or whether the water is caused to flow and/or be agitated, as is understood by one of skill in the art. In some embodiments, step (b) can proceed for from about 1 hour to about 2 weeks. In some embodiments, step (b) can proceed for from about 12 hours to about 120 hours. In some embodiments, step (b) can proceed for from about 24 hours to about 96 hours. In some embodiments, step (b) can proceed for about 72 hours. The water used in step (b) can be, e.g. distilled water, deionized water, and/or sterile water. In some embodiments, the water can be distilled water. In some embodiments, the water can further comprise, e.g. a buffer, a preservative, and/or an agent. In some embodiments, the water can be removed and replaced with a fresh volume of water at least once during step (b). In some embodiments, the water can be continually removed and replaced with fresh volumes of water during step (b), e.g. a continuous flow of water over, around, and/or through the composition can be provided.

The compositions described herein can be used to increase wound healing and/or tissue regeneration. Accordingly, the compositions described herein can be provided in a sterile condition prior to implantation in a subject. In some embodiments, the composition can be produced under sterile conditions. In some embodiments, the composition can be sterilized after it is formed. Any method of sterilization known in the art can be used, e.g. autoclaving, gamma irradiation or e-beam sterilization.

In some embodiments, the composition can be produced in a linear shape. In some embodiments, the composition can be produced in a planar shape. In some embodiments, the composition can be produced in a contoured shape. In some embodiments, the composition can be produced in a tubular chape.

The compositions can be provided in a multitude of sizes and shapes to suit particular applications, e.g. a size and shape appropriate for treating a bladder defect, and/or a size and shape appropriate for treating a bone defect. Alternatively, the compositions described herein can be cut and/or formed by a medical professional for individual applications, e.g. a 4"×4" sheet of a composition as described herein can be cut to fit a 2" diameter circular wound. In some embodiments, the porous layer can also be reduced in thickness, e.g. by cutting or slicing, to achieve the total desired thickness, e.g. a thickness which is approximately the same as the tissue into which the composition is to be implanted. The size and shape necessary for particular wound healing and/or tissue regeneration applications can be readily determined by one of skill in the art.

In some embodiments, the methods described herein can comprise adding an agent to at least one layer. In some embodiments, the agent can be a therapeutic agent. Non-limiting examples of agents are described above herein.

In some embodiments, the matrix and/or impermeable layer comprise silk fibroin. Silk fibroin can be modified after a matrix and/or impermeable layer is formed and/or after an agent is added to the layer. In some embodiments, after formation of the silk matrix and/or impermeable layer, the method can further comprise exposing the silk matrix and/or impermeable layer to a post-treatment that will affect at least one silk fibroin property. For example, post-treatment of a silk material can affect silk fibroin properties including beta-sheet content, solubility, active agent loading capacity, degradation time, active agent permeability or any combinations thereof. In some embodiments, a layer comprising silk fibroin can be caused to form beta-sheets, e.g. after an agent has been added to the layer. Silk post-processing options, e.g., to increase beta-sheet content, include, but not limited to, controlled slow drying (Hu et al. Biomacromolecules 2011 12:1686-1696; Lu et al., 10 Biomacromolecules 1032 (2009)), water annealing (Jin et al., Water-Stable Silk Films with Reduced β-Sheet Content, 15 Adv. Funct. Mats. 1241 (2005); and Hu et al. Biomacromolecules 2011 12:1686-1696), stretching (Demura & Asakura, Immobilization of glucose oxidase with *Bombyx mori* silk fibroin by only stretching treatment and its application to glucose sensor, 33 Biotech & Bioengin. 598 (1989)), compressing, and solvent immersion, including methanol (Hofmann et al., 2006), ethanol (Miyairi et al., 1978), glutaraldehyde (Acharya et al., 2008) and 1-ethyl-3-(3-dimethyl aminopropyl) carbodiimide (EDC) (Bayraktar et al., 2005); pH adjustment (see, e.g., U.S. Patent App. No. US2011/0171239, the content of which is incorporated herein by reference), heat treatment, shear stress (see, e.g., International App. No.: WO 2011/005381, the content of which is incorporated herein by reference), sonication (see, e.g., U.S. Pat. App. No. U.S. 2010/0178304; PCT/US2010/036841; and International App. No.: WO 2008/150861, the contents of which are incorporated herein by reference), and any combinations thereof. See, e.g., WO/2004/062697; WO 2008/127404; Wang et al., 36 Intl. J. Biol. Macromol. 66-70 (2005); and Kim et al., 5 Biomacromol. 786-92 (2004); Matsumoto et al., 110 J. Phys. Chem. B 21630-38 (2006). Each of the foregoing references is incorporated by reference herein in its entirety.

In one aspect, described herein is a method for wound healing or repair of a tissue defect, the method comprising applying a composition as described herein to the wound or tissue defect. Non-limiting examples of wounds and/or tissue defects can include a skin wound or defect; a diabetic ulcer; a bone wound or defect; a joint wound or defect; a meniscus wound or defect; an articular cartilage wound or defect; a soft tissue wound or defect; a lung tissue wound or defect; a burn; a liver wound or defect; a pancrease wound or defect; a gallbladder wound or defect; a kidney wound or defect; a heart wall wound or defect; and/or a vascular tissue wound or defect. In some embodiments, the wound or defect can be the result of injury or disease (e.g. trauma or degenerative disease). In some embodiments, the wound or defect can be surgically created, e.g. an incision or surgical removal of excess, damaged, or pathological tissue or material (e.g. removal of a tumor).

In some embodiments, the compositions described herein can be used to treat spinal wound or defects, e.g. intravertebral disc wounds or defects. In some emboidments, the composition described herein can be provided with in a flexible sheet or tube and positioned to be positioned around the spinal column, e.g. with the impermeable layer oriented next to the spine and the matrix layer oriented on the outer surface of the composition when placed on the spinal column. Without wishing to be bound by theory, the matrix layer can provide load bearing properties whiel the impermeable layer does not stick or or become tethered to the spinal column.

Wounds to be treated include open or closed, or as either acute or chronic in origin. In one embodiment, the compositions can be used to treat an open wound. Open wounds include, but are not limited to, incisions or incised wounds; lacerations or irregular tear-like wounds caused by some blunt trauma; avulsion; abrasions (grazes) such as superficial wounds in which the topmost layer of the skin (the epidermis) is scraped off; puncture wounds such as those caused by an object puncturing the skin; penetration wounds such as those caused by an object entering and coming out from the skin; and gunshot wounds. The wounds to be treated here can also include closed wounds such as contusions, hematomas, crush injury, chronic or acute wounds.

In some embodiments, the impermeable layer can be oriented to prevent the movement of material into or out of the wound or defect. By way of non-limiting example, the impermeable layer can prevent fluids and/or contaminants from entering a wound (e.g. preventing dirt from entering the skin or preventing fluids from entering the lung), and/or the impermeable layer can prevent fluids and/or materials from exiting a tissue via the wound or defect (e.g. preventing fluids from leaking out of the bladder or intestines via a defect or wound).

In some embodiments, the compositions can be placed on a wound or defect. In some embodiments, the compositions can be attached to the site of a wound or defect, e.g. by suturing, stapling, and/or the use of adhesives. One of skill in the art can readily determine how to secure a composition as described herein to a particular wound and/or tissue defect.

The compositions described herein, by virtue of the differing properties of the multiple layers, can provide a scaffold for tissue regeneration while at the same time, sealing the contents of a hollow organ in and/or preventing entry of fluids and/or particles (e.g. debris) into the region the composition is covering. Accordingly, in some embodiments, the wound or tissue defect is located in a hollow organ. Non-limiting examples of hollow organs include the bladder; a portion of the gastrointestinal tract; the stomach, and the intestines.

In some embodiments, the composition can be applied to a wound and/or defect in a bone. The bilayer compositions described herein mimic the differences and orientation of the compact and spony bone tissues, thereby promoting tissue regeneration of the bone tissue.

In some embodiments, the compositions described herein can be used to promote wound healing or repair of a tissue defect at a load-bearing joint. The qualitatively different degrees of surface roughness of the compositions described herein (e.g. a silk fibroin film is smoother than a silk fibroin foam) can provide a smooth surface for lubrication in joints while the rougher surface can cushion impacts and provide for host tissue integration. The same advantages are applicable to meniscus and articular cartilage repair.

The invention also provides kits and device containing the biomaterials and/or compositions described herein and instructions to carry out any of the methods described herein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "increased", "increase", or "enhance" are all used herein to mean an increase by a statically significant amount. In some embodiments, the terms "increased", "increase", or "enhance" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of wound healing. A subject can be male or female.

A "subject in need" of treatment for a particular condition can be a subject having that condition, diagnosed as having that condition, or at risk of developing that condition.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. a wound or tissue defect. The term "treating" includes reducing or alleviating at least one adverse effect or symptom of a condition, disease or disorder associated with a wound or tissue defect. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A composition comprising a first and second layer;
   the first layer comprising a porous biomaterial matrix; and
   the second layer comprising a impermeable biomaterial.
2. The composition of paragraph 1, wherein the matrix is a structure selected from the group consisting of:
   foams; hydrogels; electrospun fibers; gels; fiber mats; sponges; 3-dimensional scaffolds; non-woven mats; woven materials; knit materials; fiber bundles; and fibers.
3. The composition of any of paragraphs 1-2, wherein the biomaterial is selected from the group consisting of:
   silk fibroin; PGA; collagen; polyethylene oxide, collagen, fibronectin, keratin, polyaspartic acid, polylysin, alginate, chitosan, chitin, and hyaluronic acid.
4. The composition of any of paragraphs 1-3, wherein the silk fibroin comprises *Bombyx mori* silk fibroin.
5. The composition of any of paragraphs 1-4, wherein the first and second layers comprise the same biomaterial.
6. The composition of any of paragraphs 1-4, wherein the first and second layers comprise different biomaterials.
7. A composition comprising a first and second layer;
   the first layer comprising a porous silk fibroin matrix; and
   the second layer comprising a impermeable silk fibroin film.
8. The composition of any of paragraphs 1-7, further comprising an agent.
9. The composition of paragraph 8, wherein the agent is selected from the group consisting of:
   an antibiotic; an agent to attract cells; a cell; a stem cell; a ligand; a growth factor; a platelet; and a component of extracellular matrix.
10. The composition of any of paragraphs 1-9, wherein the average pore size of the biomaterial matrix is at least 200 µm.
11. The composition of any of paragraphs 1-10, wherein the average pore size of the biomaterial matrix is at least 300 µm.
12. The composition of any of paragraphs 1-11, wherein the average pore size of the biomaterial matrix is at least 400 µm.
13. The composition of any of paragraphs 1-12, wherein the average pore size of the biomaterial matrix is from about 200 µm to about 600 µm.
14. The composition of any of paragraphs 1-13, wherein the average pore size of the biomaterial matrix is from about 300 µm to about 500 µm.
15. The composition of any of paragraphs 1-14, wherein the average pore size of the biomaterial matrix is about 400 µm.
16. The composition of any of paragraphs 1-15, wherein the average pore size of the biomaterial matrix is about 300 µm.
17. The composition of any of paragraphs 1-16, wherein the impermeable layer is from about 10 µm to about 600 µm thick.
18. The composition of any of paragraphs 1-17, wherein the impermeable layer is from about 100 µm to about 400 µm thick.
19. The composition of any of paragraphs 1-18, wherein the impermeable layer is from about 150 µm to about 250 µm thick.
20. The composition of any of paragraphs 1-19, wherein the impermeable layer is from about 25 µm to about 150 µm thick.
21. The composition of any of paragraphs 1-20, wherein the impermeable layer is about 200 µm thick.
22. The composition of any of paragraphs 1-21, wherein the composition is from about 0.01 cm to about 5 cm thick.
23. The composition of any of paragraphs 1-22, wherein the composition is from about 0.1 cm to about 3 cm thick.
24. The composition of any of paragraphs 1-23, wherein the composition is from about 0.1 cm to about 2 cm thick.
25. The composition of any of paragraphs 1-24, wherein the composition is about 1 cm thick.
26. The composition of any of paragraphs 1-25, wherein the composition has a shape selected from the group consisting of:
    a sheet; a tube; and a contoured sheet.
27. A method of producing a composition of any of paragraphs 1-26, the method comprising;
    contacting a porous biomaterial matrix with a impermeable biomaterial layer.
28. A method of producing a composition of any of paragraphs 1-26, the method comprising;
    (a) casting an admixture of aqueous biomaterial solution and NaCl;
    (b) contacting the composition resulting from step (a) with water.
29. The method of paragraph 28, wherein step (a) is performed with the solution in contact with a pre-existing impermeable biomaterial layer.
30. The method of any of paragraphs 28-29, wherein the NaCl is granular.
31. The method of any of paragraphs 28-30, wherein the biomaterial solution is a silk fibroin solution.
32. The method of any of paragraphs 28-31, wherein the silk fibroin solution has a concentration of from about 2% wt/vol to about 15% wt/vol.
33. The method of any of paragraphs 28-32, wherein the silk fibroin solution has a concentration of from about 4% wt/vol to about 10% wt/vol.
34. The method of any of paragraphs 28-33, wherein the silk fibroin solution has a concentration of about 6% wt/vol.

35. The method of any of paragraphs 28-34, wherein the admixture is cast for from about 12 hours to about 96 hours.
36. The method of any of paragraphs 28-35, wherein the admixture is cast for from about 24 hours to 72 hours.
37. The method of any of paragraphs 28-36, wherein the admixture is cast for about 48 hours.
38. The method of any of paragraphs 28-37, wherein step (b) proceeds for from about 12 hours to about 120 hours.
39. The method of any of paragraphs 28-38, wherein step (b) proceeds for from about 24 hours to about 96 hours.
40. The method of any of paragraphs 28-39, wherein step (b) proceeds for about 72 hours.
41. The method of any of paragraphs 28-40, wherein the water is distilled water.
42. The method of any of paragraphs 28-41, wherein the water is removed and replaced with a fresh volume of water at least once during step (b).
43. The method of any of paragraphs 28-42, wherein, during the casting step, the admixture of biomaterial solution and NaCl is in contact with an impermeable layer.
44. The method of any of paragraphs 27-43, wherein the impermeable biomaterial layer comprises silk fibroin.
45. The method of any of paragraphs 27-44, wherein the method further comprises a first step of casting silk fibroin solution to form an impermeable silk fibroin layer.
46. The method of paragraph 45, wherein the silk fibroin solution has a concentration of from about 2% wt/vol to about 15% wt/vol.
47. The method of paragraph 45, wherein the silk fibroin solution has a concentration of from about 4% wt/vol to about 10% wt/vol.
48. The method of paragraph 45, wherein the silk fibroin solution has a concentration of about 8% wt/vol.
49. The method of any of paragraphs 27-48, wherein the composition is produced under sterile conditions or sterilized after the rinsing step is complete.
50. The method of any of paragraphs 27-49, wherein the composition is produced in a linear shape.
51. The method of any of paragraphs 27-50, wherein the composition is produced in a tubular shape.
52. The method of any of paragraphs 27-51, wherein the method further comprises adding an agent to at least one layer.
53. The method of paragraph 52, wherein the agent is a therapeutic agent.
54. The method of any of paragraphs 27-53, wherein the method further comprises altering the β-sheet content of a silk fibroin layer.
55. The method of paragraph 54, wherein the β-sheet content of a silk fibroin layer is altered using a method selected from the group consisting of:
    contacting the layer with water vapor; drying; dehydration; water annealing; stretching; compression; solvent immersion; immersion in methanol; immersion in ethanol; pH adjustment; heat treatment; and sonication.
56. The method of any of paragraphs 54-55, wherein the β-sheet content of a silk fibroin layer is altered after adding an agent to the layer.
57. A method for wound healing or repair of a tissue defect, the method comprising applying a composition of any of paragraphs 1-26 to the wound or tissue defect.
58. The method of paragraph 57, wherein the wound or tissue defect is located in a hollow organ.
59. The method of paragraph 58, wherein the hollow organ is selected from the group consisting of:
    the bladder; a portion of the gastrointestinal tract; the stomach, and the intestines.
60. The method of paragraph 57, wherein the wound or tissue defect is selected from the group consisting of:
    a skin wound or defect; a diabetic ulcer; a bone wound or defect; a joint wound or defect; a meniscus wound or defect; an articular cartilage wound or defect; a soft tissue wound or defect; a lung tissue wound or defect; and a kidney wound or defect.
61. The method of any of paragraphs 57-60, wherein the impermeable layer is oriented to prevent the movement of material into or out of the wound or defect.

EXAMPLES

Example 1

Bi-Layer Silk Sheet for Hollow Organ Repair

Described herein is a 3-D biomaterial composed of silk fibroin derived from *Bombyx mori* silkworm cocoons. This scaffold is composed of a bi-layer structure consisting of one porous layer buttressed by a thin non-permeable, barrier layer. This scaffold is intended for use, for example, in the repair of hollow organ defects such as the urinary bladder in procedures such as augmentation cystoplasty. The composition's bi-layer structure permits, e.g. retention of hollow organ contents (i.e. urine) following initial implantation into defect sites while the porous layer allows for host tissue ingrowth during defect consolidation.

Preparation of Silk Solutions:

*B. mori* silkworm cocoons were boiled for 20 min in an aqueous solution of 0.02M Na2CO3 and then rinsed thoroughly with distilled water to extract the glue-like sericin proteins and wax. The extracted silk fibroin was then dissolved in 9.3M LiBr solution at 60 C for 6 h. This solution was dialyzed in distilled water using a Slide-a-lyzer dialysis cassette (MWCO, 3500) for 4 d yielding an 8% (wt/vol) aqueous silk fibroin solution (See e.g., Kim et al., 2004; which is incorporated by reference herein in its entirety). Two methods of casting the resultant silk matrix are described below.

Preparation of Matrix:

Method 1:

A variant of a previously published solvent casting/salt leaching technique was used (Kim et al., 2004). 75 ml of an aqueous silk fibroin solution (6% wt/vol) was poured into a rectangular casting vessel (12 cm×10 cm) and granular NaCl (150 g, 500-600 μM average crystal size) was mixed with the silk solution. The resultant solution was allowed to cast for 2 d at room temperature and then NaCl was removed by washing in distilled water for 2 d. Spontaneous formation of the bi-layer scaffold was achieved. Scanning electron microscopy and tensile testing was used to determine structural and mechanical properties (FIG. 1).

Figure 2:
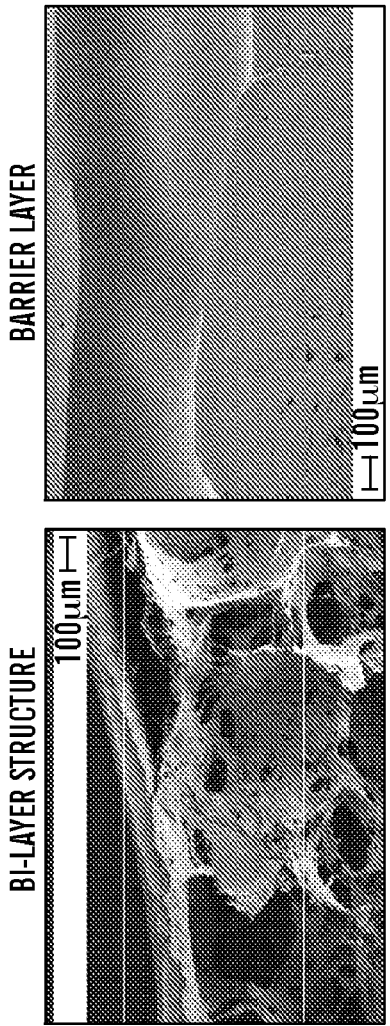
FIG. 2 depicts scanning electron microscopy analysis and tensile testing of the structural and mechanical properties of bilayer compositions produced according to Method 2 of Example 1.

Method 2:

20 ml of an aqueous silk fibroin solution (8% wt/vol) was poured into a rectangular casting vessel (12 cm×10 cm) and dried in a laminar flow hood to achieve formation of a silk film. Next as described above, 75 ml of an aqueous silk fibroin solution (6% wt/vol) was poured into the rectangular casting vessel (12 cm×10 cm) and granular NaCl (150 g, 500-600 μM average crystal size) was mixed with the silk solution on top of the silk film. The resultant solution was allowed to cast for 2 d at room temperature and then NaCl was removed by washing in distilled water for 2 d. Fusion of the silk film and bulk matrix occurred to generate bi-layer scaffold. Scanning electron microscopy and tensile testing was used to determine structural and mechanical properties (FIG. 2).

Figure 3:
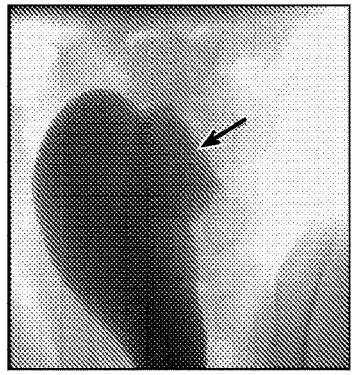
FIG. 3 depicts cystogram images of bladders at 1 and 3 months post-implatation.
Figure 3:
Figure 4:
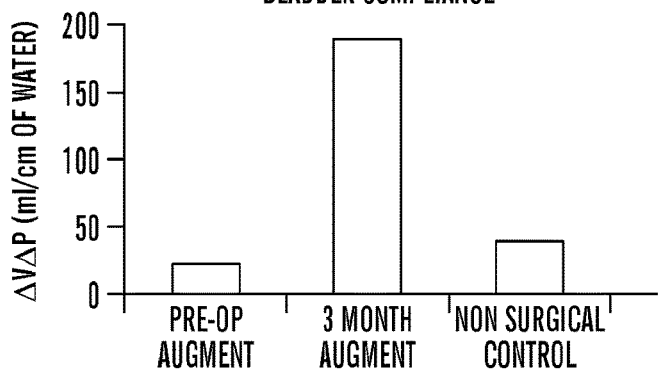
FIG. 4 depicts urodynamic assessment of silk augmented bladder at 3 months of implantation in comparison to non augmented controls.
Figure 4:
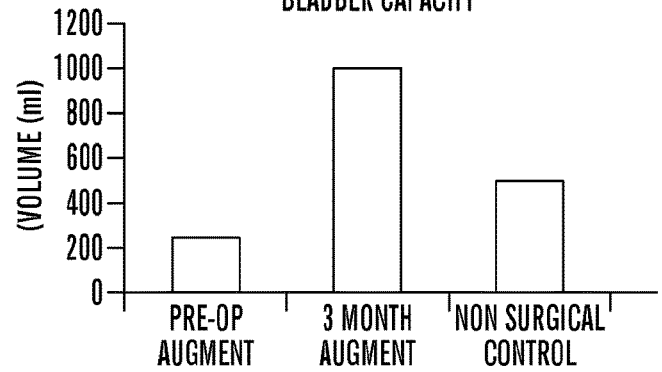

Surgical Evaluations:

Robotic augmentation cystoplasty procedure used to validate the performance of silk matrix produced in Method 1. Scaffold was implantation for 3 months in which animal was catheterized for 1 week post-op and then allowed to spontaneously void. The structure of augmented porcine bladder structure and kidneys following 3 months of silk matrix implantation was examined. No evidence of hydronephrosis was observed. Histological and immunohistochemical analyses of regenerated bladder tissue supported by silk matrix following 3 months of implantation were performed, comparing the regenerated tissue to non augmented regions of bladder tissue. Regenerated tissue displayed morphology mimicking that of the non-augmented regions, as well as displaying α-actin, uroplakin, p63, cytokeratin, and SM22α expression, both at the periphery and center of the regenerated tissue (data not shown). Furthermore, the silk matrix was observed to degrade over the course of implantation (data not shown and FIG. 3). FIG. 4 depicts urodynamic assessment of silk augmented bladder at 3 months of implantation in comparison to non augmented controls.

Example 2

The Effect of Matrix Processing Techniques on the Performance of Silk Scaffolds in a Rat Model of Augmentation Cystoplasty Congenital and acquired urinary tract pathologies such as neurogenic bladder, bladder exstrophy, and posterior urethral valves routinely require enterocystoplasty in order to reduce urinary storage and voiding pressures and mitigate the risk of renal damage and incontinence. Although the use of autologous gastrointestinal segments represents the gold standard of care for bladder reconstruction, this strategy is associated with significant complications including chronic urinary tract infection, metabolic abnormalities, and secondary malignancies. Biomaterials including acellular bladder matrix, small intestinal submucosa (SIS), and poly-glycolic acid (PGA), either alone or seeded with primary or progenitor bladder cell sources, have been previously explored as alternatives for bladder defect repair in a variety of animal models as well as short-term clinical studies. Despite the ability of these matrices to support bladder tissue regeneration, restoration of organ function is often hindered by suboptimal scaffold properties which frequently lead to long-term graft failure due to implant contracture, graft rupture, and/or fibrosis. Therefore, there is a major clinical need to develop novel scaffold configurations which can overcome these limitations and thus serve as viable options for bladder tissue engineering.

Silk fibroin-based biomaterials encompass a unique array of properties including high structural strength and elasticity, diverse processing plasticity, and tunable biodegradability which make them well suited for the consolidation of hollow organ defects. As described herein, the performance of silk biomaterials was evaluated in a rat model of augmentation cystoplasty. The ability of various 3-D scaffold configurations produced from different processing techniques, including gel spinning or solvent casting/salt leaching, were compared for their potential to support bladder tissue repair and functional voiding responses. It was hypothesized that NaCl-leaching of aqueous-based silk fibroin solutions may offer particular advantages over gel spinning for the construction of biomaterials for bladder tissue engineering.

By manipulating the NaCl crystal diameter, the solvent casting/salt leaching method allows for greater scalability of scaffold pore size (470-940 µm) [Kim et al., 2005] in relation to lyophilization of gel spun matrices which routinely generates pore diameters below 200 µm. In addition, lower concentrations of silk fibroin solutions are utilized for the formation of NaCl-leached scaffolds (<10% wt/vol) in comparison to the gel spun spinning technique which requires solutions containing 20-30% wt/vol for scaffold fabrication. A systematic analysis of the impact of processing methods on the ability of silk scaffolds to support bladder tissue regeneration is a crucial step in the development of biomaterial configurations for clinical organ repair.

Materials and Methods

Biomaterials.

Aqueous silk fibroin solutions were prepared from *Bombyx mori* silkworm cocoons using previously described procedures [Kim et al., 2005]. Three distinct groups of silk-based matrices were fabricated from these solutions by either a gel spinning technique [Lovett et al., 2008] or a solvent-casting/salt-leaching method [Kim et al., 2005]. Gel spun scaffolds were produced by spinning concentrated silk solutions [25-30% (wt/vol), 0.5 ml/scaffold] onto a rotating (200 rpm) and axially reciprocating mandrel (6 mm in diameter) using a custom gel spinning platform and program. Two groups of matrices previously shown to support murine bladder augmentation, but with different structural and mechanical properties, were generated with various winding and post-winding conditions using this method [Mauney et al., 2011; Gomez et al., 2011]. GS1 matrices were spun with an axial slew rate (ASR) of 2 mm/sec followed by treatment with methanol. GS2 scaffolds were composed of ~0.4 ml of silk solution spun at an ASR of 40 mm/sec followed by ~0.1 ml spun at 2 mm/sec in order to consolidate gaps between the resultant silk fibers. This matrix group was then subjected to lyophilization and subsequent methanol treatment. The FF scaffold group was composed of 3-D porous silk foams which were annealed to silk films on their top external face. Briefly, a silk fibroin solution (8% wt/vol) was poured into a rectangular casting vessel and dried in a laminar flow hood for 48 h to achieve formation of a silk film. A 6% wt/vol silk fibroin solution was then mixed with sieved granular NaCl (500-600 µM average crystal size) and layered on to the surface of the silk film. The resultant solution was allowed to cast for 48 h and NaCl was subsequently removed by washing the scaffold for 72 h in distilled water with regular volume changes. Fusion of the silk film with the bulk foam matrix occurred to generate a bi-layer scaffold configuration. Silk matrix groups were then sterilized in 70% ethanol, rinsed in phosphate buffered saline (PBS) overnight, and subjected to analytical or surgical procedures described below. Small intestinal submucosa (SIS) (Cook, Bloomington, Ind.) scaffolds were evaluated in parallel as standard points of comparison since this biomaterial has been previously deployed in bladder augmentation approaches in both animal and human models [Kropp et al., 1998; Caione et al., 2012].

Scanning Electron Microscopy (SEM).

Structural analysis of matrix groups was performed in order to assess differences in scaffold morphology generated by various fabrication techniques. Matrix samples were sputter coated with gold and imaged using a Hitachi S-520 Scanning Electron Microscope.

Mechanical Testing.

Uniaxial tensile tests were performed as previously described [Gomez et al., 2011] on an Instron 3366 testing frame (Norwood, Mass.) equipped with a 100 N capacity load cell and Biopuls pneumatic clamps. Matrix groups (N=3-4 per group) were hydrated in PBS for at least 24 h to reach a swelling equilibrium prior to testing. Test samples were submerged in a temperature-controlled testing container (Biopuls) filled with PBS (37° C.). A displacement control mode with a crosshead displacement rate of 5 mm/min was used, and the gauge length was 15 mm. The initial elastic modulus (EM), ultimate tensile strength (UTS) and % elongation to failure were calculated from stress/strain plots. EM was calculated by using a least-squares (LS) fitting between 0.02 N load and 5% strain past this initial load point. UTS was determined as the highest stress value attained during the test and the % elongation to failure was the last data point before a >10% decrease in the load.

Rat Bladder Augmentation.

Biomaterial groups were evaluated in a bladder augmentation model using adult female immunocompetent Sprague Dawley rats (6 weeks old, Charles River Laboratories, Wilmington, Mass.) following IACUC approved protocols as previously described [Tu et al., 2012]. Briefly, animals were anesthetized using isoflurane inhalation and then shaved to expose the surgical site. A low midline laparotomy incision was then made and the underlying tissue (rectus muscle and peritoneum) was dissected free to expose the bladder. The anterior portion (immediately distal to the dome) of the bladder was marked with 7-0 polypropylene (Prolene) sutures in a square configuration. A longitudinal cystotomy incision was then made in the anterior bladder wall in the middle of these holding sutures using fine scissors to create a bladder defect. A square piece of biomaterial (7×7 mm$^2$) was then anastamosed to this site using a 7-0 vicryl continuous suture. In addition, a control group of animals receiving a cystotomy alone were treated similarly. A watertight seal was confirmed by filling the bladder with sterile saline via instillation through a 30 gauge hypodermic needle. Matrix and control groups were assessed independently for 10 weeks of implantation with animals subsequently subjected to cystometric, histological and immunohistochemical analyses described below.

Cystometric Analyses.

Bladder urodynamics were evaluated in all rodents using conscious unrestrained cystometry at 10 weeks post implantation as previously described [Tu et al., 2012]. A suprapubic catheter was surgically inserted in the bladder prior to this. After induction with isoflurane anesthesia, the animals were prepped and draped in a sterile fashion. A dorsal midline incision was made in between the scapulae of the rats. A laparotomy was created using a ventral midline incision. Polyethylene-50 tubing with a flared tip was tunneled from the dorsal incision into the peritoneal cavity. A purse-string 6-0 prolene stitch was used to secure the flared tip of the polyethylene-50 tubing into the dome of the bladder. The exteriorized polyethylene-50 tubing on the dorsal aspect was attached to a luer lock adapter and secured to the skin with a 3-0 silk suture. Cystometry was conducted 1-3 d after suprapubic catheter placement. The suprapubic catheter was attached to a physiological pressure transducer (model MLT844, ADInstruments, Colorado Springs, Colo.) to allow measurement of intravesical pressure, while the bladder was continuously infused with sterile PBS at 100 µl/min. Post void residual volume was measured by aspirating the suprapubic catheter at the conclusion of cystometry. After establishment of a regular voiding pattern, multiple other variables were extrapolated from the cystometric tracings, such as compliance, voided volume, peak voiding pressure, inter-contraction interval and spontaneous non voiding contractions (SNVC). A total of 6 animals per group with 4 voids per animal were analyzed to determine urodynamic parameters.

Histological and Immunohistochemical Analyses.

Following 10 weeks of implantation, animals were euthanized by $CO_2$ asphyxiation and bladders were excised for standard histological processing. Briefly, organs were fixed in 10% neutral-buffered formalin, dehydrated in graded alcohols, and then embedded in paraffin in an axial orientation to capture the entire circumferential surface of the bladder within each section. Correct orientation (anterior vs posterior) within the paraffin block was determined by suture placement on the specimen. Sections (10 µm) were cut and then stained with hematoxylin and eosin (H&E) or Masson's trichrome (MTS) as previously described [Gomez et al., 2011]. For immunohistochemical (IHC) analysis, contractile smooth muscle markers such as α-smooth muscle actin (α-SMA) and SM22α; urothelial-associated proteins, uroplakins (UP) and p63; neuronal and endothelial markers, Fox3 and CD31, respectively were detected using the following primary antibodies: anti-α-SMA [Sigma-Aldrich, St. Louis, Mo., cat. # A2457, 1:200 dilution], anti-SM22a [Abcam, Cambridge, Mass., cat. # ab14106, 1:200 dilution], anti-pan-UP [rabbit antisera raised against total bovine UP extracts, 1:100 dilution], anti-p63 [Santa Cruz Biotechnology, Santa Cruz, Calif., cat. # sc-8431, 1:200 dilution], anti-Fox3 [Abcam, cat. # ab104225, 1:200 dilution], anti-CD31 [Abcam, cat. # ab228364, 1:100 dilution]. Sections were then incubated with species-matched Cy3-conjugated secondary antibodies (Millipore, Billerica, Mass.) and nuclei were counterstained with 4', 6-diamidino-2-phenyllindole (DAPI). Specimens were visualized using an Axioplan-2 microscope (Carl Zeiss MicroImaging, Thornwood, N.Y.) and representative images were acquired using Axiovision software (version 4.8).

Statistical Analysis.

Urodynamic measurements were analyzed by generalized estimating equations with post-hoc Bonferroni testing using commercially available statistical software (SAS9.3 software, www.sas.com). Statistically significant values were defined as $p<0.05$. Urodynamic parameters are displayed as means±standard deviation.

Results and Discussion

Figures 5A, 5B:
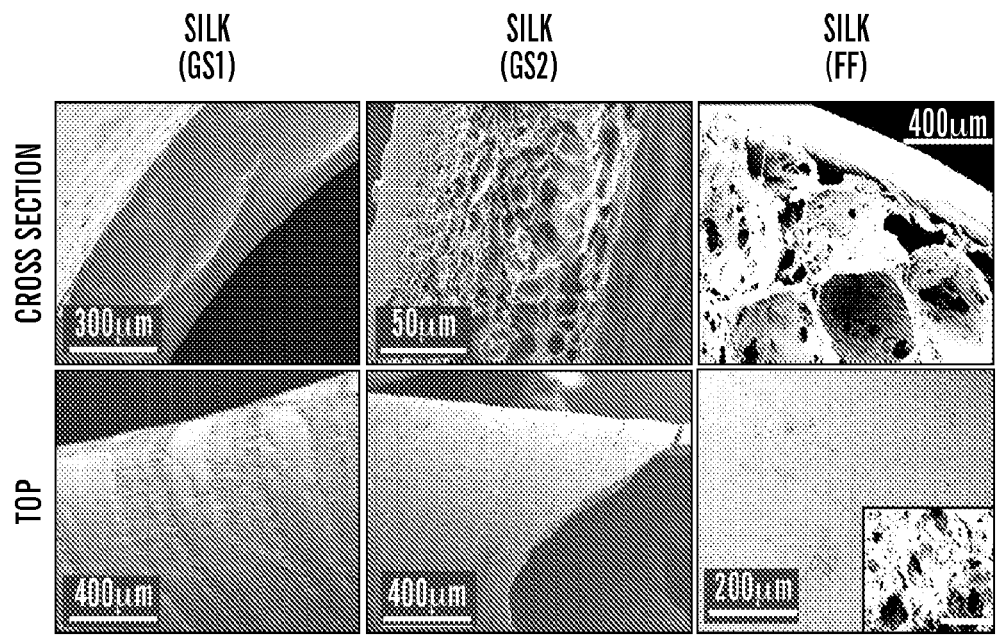
FIGS. 5A-5B depict the results of structural and mechanical analyses of scaffold groups.

SEM analyses of silk matrix groups revealed that scaffold processing techniques as well as distinct fabrication parameters led to selective differences in overall biomaterial structural architecture (FIG. 5A). As observed in previous studies [Mauney et al., 2011; Gomez et al., 2011; Franck et al., 2013], GS1 scaffolds consisted of compact multi-laminates of parallel-oriented silk fibers while GS2 matrices were composed of porous (pore size range, 5-50 µm) lamellar-like sheets buttressed by a dense outer layer. In contrast, FF scaffolds consisted of a bi-layer structure with compartments dictated by the mode of fabrication. The solvent-casting/NaCl-leached layer comprised the bulk of the matrix and resembled a foam configuration with large pores (pore size, ~400 µm) interconnected by a network of smaller pores dispersed along their periphery. This layer was fused on the external face with a homogeneous, nonporous silk film (200 µm thick) generated by the annealing of dehydrated silk solutions during matrix casting. Pore occlusion of the solvent cast/NaCl-layer was also observed in the bulk matrix along the plane adjacent to the casting vessels in scaffolds produced in the absence of silk films (data not shown); however continuity of this feature was heterogeneous along the surface area as well as highly variable between matrix replicates. Tensile testing of FF scaffolds prior to implantation (FIG. 5B) demonstrated a lower degree of UTS and EM compared to the previously published properties of both gel spun matrix configurations [Gomez et al., 2011]. SIS scaffolds exhibited substantially higher UTS and EM in comparison to all silk groups. Elongation to failure measurements revealed that the FF group was ~4 fold more elastic than any other matrix configuration tested suggesting that although these scaffolds had lower respective UTS they could achieve larger degrees of deformation; a potential advantage for the consolidation of highly distensible bladder defects.

The porous foam compartment of the FF scaffold configuration independent of the annealed silk film was first analyzed for its potential to support bladder defect integration within the rat model of augmentation cystoplasty. During initial implantation, poor degrees of scaffold suture retention were noted leading to dehiscence at the suture line between the matrix and the bladder wall. In addition, ex vivo assessments of initial defect closure following surgical integration demonstrated prominent fluid leaks within center of the scaffold coupled with a failure of the implant to support bladder distension during saline instillation. The inability of silk foams to restore the integrity of defect sites is presumably due to the interconnected porous nature of this scaffold type which was insufficient to mimic the barrier function of the native bladder wall following a rise in intravesical pressure. In contrast, FF scaffolds consisting of silk films annealed to the exterior face of the porous silk foams were observed to support organ integrity and distension following surgical integration similar to the performance of gel spun silk scaffold configurations and SIS. These results demonstrate that the annealed silk film compartment is essential for the bi-layer FF group to maintain initial defect consolidation within this model system.

Over the course of the 10 week implantation period, survival rates of the augmented animals in 3 out of 4 scaffold groups were similar to cystotomy controls prior to scheduled euthanasia. Bladder reconstruction with GS1 and FF groups displayed survival rates of 100% (10/10 for GS1 and 8/8 for FF) while animals implanted with SIS exhibited an 88% survival rate (8/9); both values were comparable to the 90% rate observed following cystotomy alone. In contrast, animals implanted with GS2 scaffolds displayed a reduced rate of survival at 60% (9/15). All spontaneous animal deaths in each group occurred within the first post-operative week and post-mortem analyses revealed urinary ascites as the probable cause in all cases due to scaffold perforation. Previous reports deploying GS2 matrices for murine bladder augmentation demonstrated a 100% survival rate (6/6), however the greater tendency for animal death from scaffold urine leaks observed in this study is presumably related to the increase in scaffold area used between the rat and murine models. The lyophilization process utilized during GS2 construction is prone to generating microfractures in the nonporous outer layer of this scaffold configuration (FIG. 5A) [Gomez et al., 2011] thereby increasing the potential for the integrity of the matrix to become compromised with increased surface area.

Figures 6A, 6B:
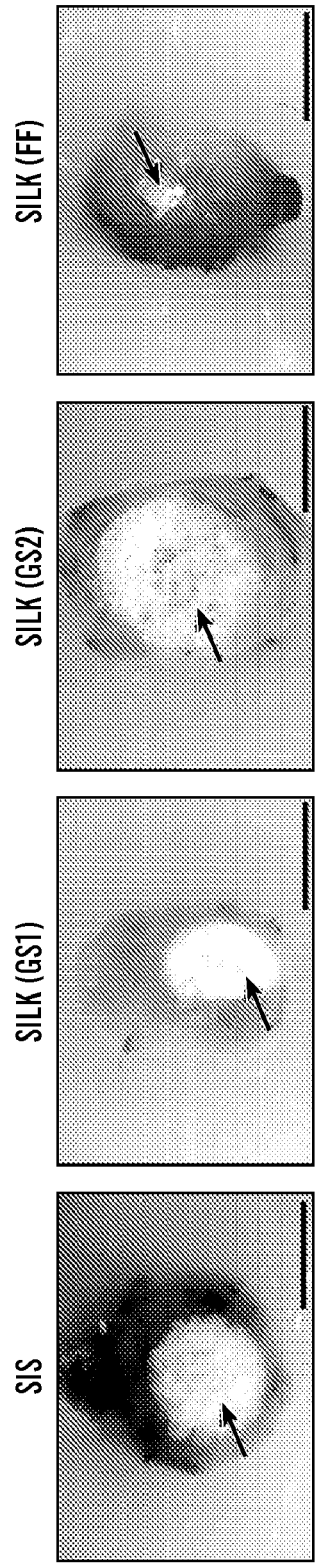
FIGS. 6A-6B depict the characterization of urinary stone incidence and size in regenerated bladders.

Following 10 weeks post-op, gross tissue evaluations of the lower urinary tract revealed no signs of bladder mucus or hydronephrosis in any of the sacrificed animals, however the presence of lumenal bladder stones was evident in all experimental groups examined (FIGS. 6A-6B). These data are consistent with other previous studies which have shown that the formation of bladder calculi is a common occurrence in rat models of bladder reconstruction with biodegradable acellular materials [Kropp et al., 1995; Vaught et al., 1996; Iijima et al., 2007]. The incidence of urinary calculi was the highest in the gel spun silk cohorts with animals augmented with GS1 and GS2 matrices exhibiting a frequency of 75% and 71%, respectively. SIS implants elicited similar extents of stone formation by comparison with a frequency of 57%. In contrast, rats subjected to cystotomy alone or FF scaffold implantation demonstrated the lowest respective incidence of stone formation at 13% and 20%. In addition, stone diameters in these groups were also found to be substantially lower (2 mm) in comparison to all other experimental conditions (3-4 mm). These results show that the frequency and extent of bladder stone formation within the rat augmentation cystoplasty model is dependent on biomaterial composition (silk versus SIS) as well as the processing method utilized for silk scaffold construction.

Histological examination of whole bladder sections (H&E and MTS) demonstrated that each scaffold group supported robust degrees of connective tissue ingrowth which traversed from the periphery of the native bladder wall to the interior of the original defect site (data not shown). Residual GS1 and GS2 matrices were localized to the bladder lumen and were primarily intact exhibiting minimal extents of degradation. These results are consistent with the gross tissue observations wherein scaffold remnants from both groups were found encapsulated within lumenal bladder stones. In contrast to our previous study [Gomez et al., 2011], the rate of in vivo scaffold degradation was not substantially elevated by the porous architecture of GS2 matrices in comparison to the non porous GS1 group. An increase in GS2 area utilized in the rat ($7 \times 7$ mm$^2$) versus the murine ($4 \times 4$ mm$^2$) model may have allowed for enhanced structural stability and therefore less fragmentation of the bulk matrix following 10 weeks of implantation. Indeed, similar relationships between degradation profiles and scale-up of scaffold dimensions have been reported for a variety of biomaterial formulations [Wu et al., 2004].

The degradation pattern of the FF scaffolds was found to be dependent on the structural architecture of the bi-layer matrix with the porous region exhibiting extensive degrees of fragmentation within the bladder wall while the non porous silk films remained largely intact. Higher initial levels of silk fibroin utilized for film construction in respect to the porous compartment may have also contributed to the observed differences in degradation profile. In addition, the enhanced rate of degradation demonstrated by the porous regions of the FF scaffolds in comparison to the GS2 matrices was presumably related to the increase in pore size as well as the lower content of silk fibroin which would have allowed for more efficient exposure of the matrix interior to proteolytic enzymes and subsequent polymer hydrolysis. Analysis of the degradation profile of collagenous SIS scaffolds revealed more extensive fragmentation in respect to all silk groups with minimal degrees of residual matrix detected within the bladder lumen. Taken together, these data demonstrate that the silk scaffolds investigated in this study are more structurally stable than SIS matrices in vivo, however alterations in the rate of silk scaffold degradation can be achieved through different scaffold processing techniques with the solvent casting/salt-leaching method encouraging increased degrees of matrix degradation in comparison to gel spinning protocols.

For each biomaterial group, H&E and MTS analyses demonstrated the presence of robust smooth muscle bundles (H&E: pink; MTS: red) localized throughout the periphery of the regenerated bladder wall (data not shown). IHC assessments revealed that the reconstituted smooth muscle layers of all scaffold groups stained positive for both α-SMA and SM22a contractile protein expression to similar extents as those observed with the cystotomy controls indicating prominent smooth muscle maturation (data not shown). No evidence of severe fibrotic events was detected in these regions in any of the experimental groups examined. In addition, an ECM-rich lamina propria populated with fibroblastic populations was also evident in the regenerated tissues supported by all matrix configurations. In comparison to cystotomy controls, histological features within the lamina propria indicative of minimally acute inflammatory reactions were noted at each implantation site characterized by the presence of disperse eosinophil granulocytes, however evidence of substantial chronic inflammatory events was not observed in response to any experimental condition.

Histological evaluations also demonstrated that each implant group supported the formation of a multi-layer urothelium covering the entire lumenal surface of the original defect site (data not shown). The transitional nature of the urothelium was confirmed in all regenerated tissues by IHC analysis wherein p63-positive basal and intermediate cell layers were lined with lumenal p63-negative superficial cells. Varying degrees of hyperplasia were observed in the basal and intermediate cell compartments supported by all implant groups in comparison to cystotomy controls. This feature may reflect incomplete urothelial maturation since normalization of basal/intermediate cell proliferation is required during wound healing for native tissue stratification to be achieved [de Boer et al., 1994; Gomez et al., 2011]. However across all matrix groups, robust pan-UP protein expression was noted in both regenerated superficial and intermediate cell layers to levels similar to those observed in control tissues. Expression and assembly of UP proteins into heterodimers which form asymmetrical unit membranes is essential for maintaining the integrity of the urothelial permeability barrier [Kong et al., 2004].

IHC analyses revealed evidence of de novo vascularization and innervation processes in the regenerated tissues supported by each implant group (data not shown). Vessels containing prominent CD31 positive endothelial cells were present throughout the original defect sites while neuronal lineages displaying Fox3 peri-nuclear protein expression were found localized to the sub-urothelial region of the regenerated bladder walls similar to cystotomy controls. These results demonstrate that silk scaffold configurations described in this study are capable of supporting regeneration of innervated, vascularized smooth muscle and urothelial tissues to levels comparable to conventional SIS matrices in a rat model of bladder defect repair.

Figure 7A:
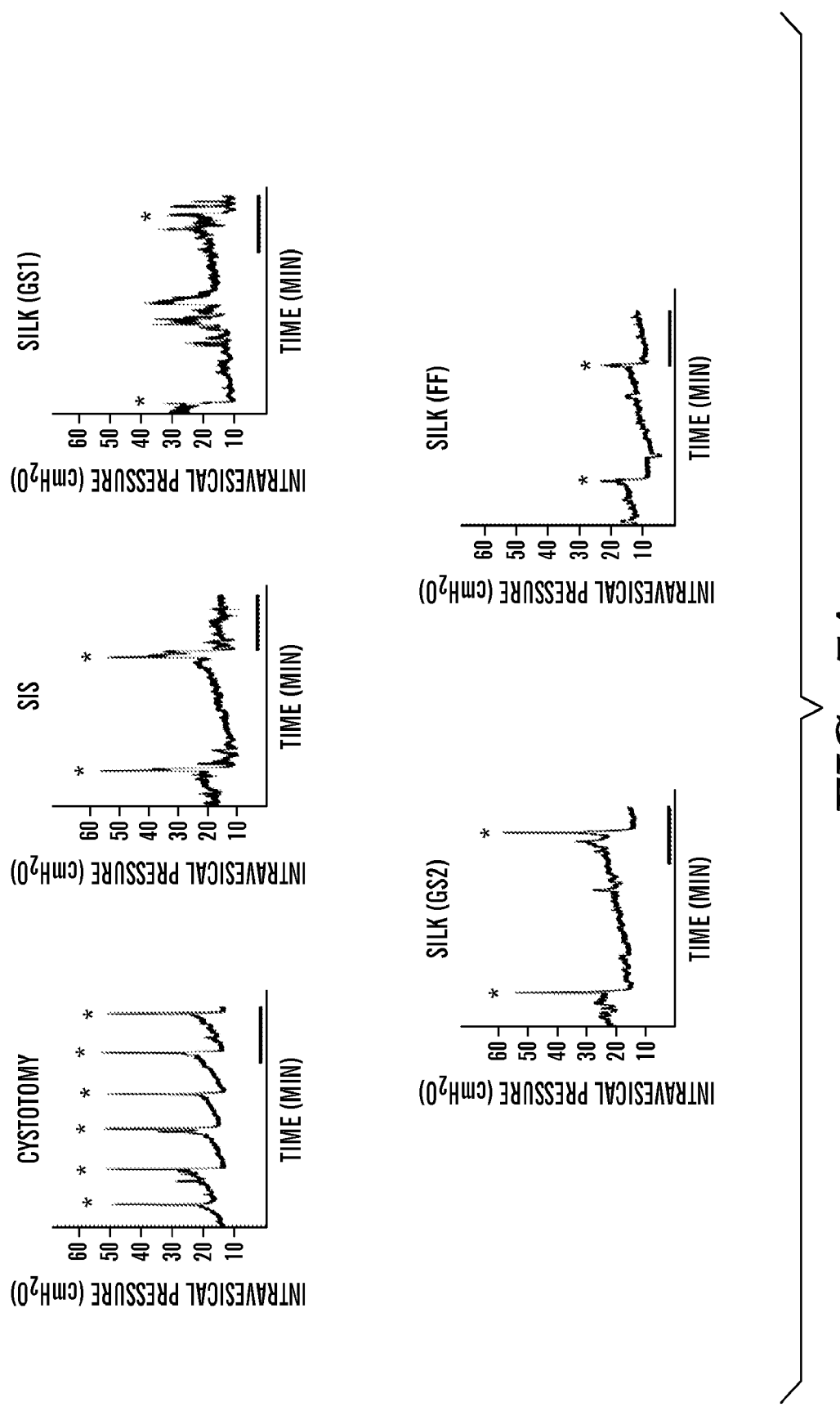

The functionality of reconstructed bladders was assessed by conscious unrestrained cystometry following 10 weeks of biomaterial implantation. Voided volume was used as a surrogate marker for bladder capacity given that post-void residual volumes were similar in each experimental group (data not shown) [Chang et al., 2009]. Rats augmented with GS1 and FF scaffolds had significantly higher mean voided volumes compared to cystotomy controls and in contrast the other scaffold groups, GS2 and SIS. In accordance with larger voided volumes, animals with GS1 and FF implants also had significantly longer intercontraction intervals compared to control levels, indicating greater functional bladder capacity since more time was required for bladder filling between voiding cycles. SNVC were used as a measure of detrusor overactivity as previously described [Abrams et al., 2003]. Rats implanted with SIS, GS1 and GS2 matrices had significantly higher numbers of SNVC compared to the cystotomy group. In contrast, animals augmented with FF scaffolds displayed SNVC levels similar to controls. The difference in SNVC is likely due to the increase in frequency and size of intra-lumenal calculi observed in the SIS, GS1, and GS2 in respect to control and FF groups since bladder stones are known to elicit organ irritation resulting in detrusor overactivity and urge incontinence [Blaivas et al., 2009]. Compliance is a measure of the ability of the urinary bladder to store large volumes of urine at low intravesical pressures. Significant gains in bladder compliance were observed in rats implanted with FF scaffolds in comparison to cystotomy controls and in contrast to all other scaffold configurations. Peak intravesical pressures however were similar between all experimental groups. These results are consistent with the ability of FF scaffolds to support bladder tissue regeneration with increased functional capacity relative to controls and distensible mechanical properties (FIGS. 7A-7B).

REFERENCES

Mauney J R, Cannon G M, Lovett M L, Gong E M, Di Vizio D, et al. (2011) Evaluation of gel spun silk-based biomaterials in a murine model of bladder augmentation. Biomaterials 32: 808-818.

Gomez P, Gil E S, Lovett M L, Rockwood D N, Di Vizio D, et al. (2011) The effect of manipulation of silk scaffold fabrication parameters on matrix performance in a murine model of bladder augmentation. Biomaterials 32: 7562-7570.

Chang S J, Yang S S. Variability, related factors and normal reference value of post-void residual urine in healthy kindergarteners. J. Urol. 2009 October; 182(4 Suppl): 1933-8. doi: 10.1016/j.juro.2009.02.086.

Abrams P. Describing bladder storage function: overactive bladder syndrome and detrusor overactivity. Urology. 2003 November; 62(5 Suppl 2):28-37; discussion 40-2.

Hofmann S, Hagenmüller H, Koch A M, Müller R, Vunjak-Novakovic G, Kaplan D L, Merkle H P, Meinel L. Control of in vitro tissue-engineered bone-like structures using human mesenchymal stem cells and porous silkscaffolds. Biomaterials. 2007 February; 28(6):1152-62. Epub 2006 Nov. 7.

Wu L, Ding J. In vitro degradation of three-dimensional porous poly(D,L-lactide-co-glycolide) scaffolds for tissue engineering. Biomaterials. 2004 December; 25(27):5821-30.

Kropp B P, Eppley B L, Prevel C D, Rippy M K, Harruff R C, Badylak S F, Adams M C, Rink R C, Keating M A. Experimental assessment of small intestinal submucosa as a bladder wall substitute. Urology. 1995 September; 46(3):396-400.

Example 3

Currently, autologous gastrointestinal segments are utilized as the primary option for bladder reconstructive procedures despite their inherent morbidity and significant complication rate. Biomaterials derived from *Bombyx mori* silk fibroin represent attractive alternatives for bladder tissue engineering given their mechanical robustness, processing plasticity, and biodegradability. As described herein, it was hypothesized that acellular silk matrices would effectively mediate tissue regeneration in a large animal model of bladder augmentation.

Methods. Scaffolds (6×6 cm²) were generated from aqueous solutions of 6% silk fibroin by a previously reported solvent casting/sodium chloride-leaching process. Scanning electron microscopy (SEM) and tensile testing were performed to ascertain structural and mechanical properties of scaffolds prior to implantation. Matrices were anastomosed to the bladder dome of Yorkshire pigs (N=6) either through open or robot-assisted augmentation cystoplasty. After an initial catheter drainage period of 7 days, pigs were allowed to void spontaneously and housed for 3 months. Cystometric analysis was used to determine bladder capacity both pre-operatively and 3 months post-op. Following euthanasia, histological (H&E and Masson's trichrome) and immunohistochemical (IHC) analyses of smooth muscle contractile protein expression (a-actin and SM22a), urothelial-associated markers (cytokeratins, p63, and uroplakins), and markers of innervation (Fox3) and vascularization (von willebrand factor (wWF)) were assessed at the periphery and center of the original implantation site as well as a nonsurgical control region. The results demonstrate that silk scaffolds support smooth muscle and urothelial regeneration as well as innervation and vascularization of the defect site. The implant periphery anc center displayed robust smooth muscle (a-actin, SM22a), urothelial (cytokeratins, p63, and uroplakins), neuronal (Fox3) and vascular regeneration (vonWBF, von willebrand factor) marker expression 3 mos post-op (data not shown).

Figure 8A:
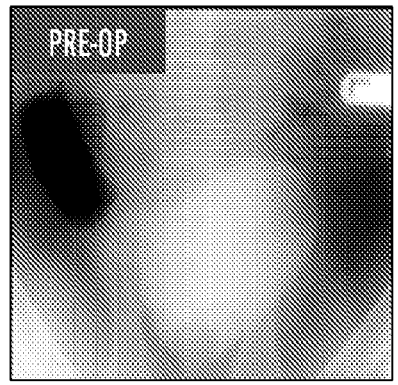
FIGS. 8A-8C demonstrate that silk augmented bladders display increases in capacity over time.
Figure 8B:
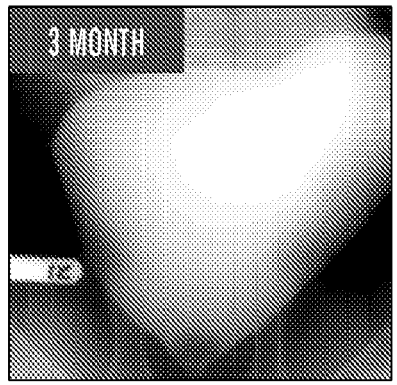
Figure 8C:
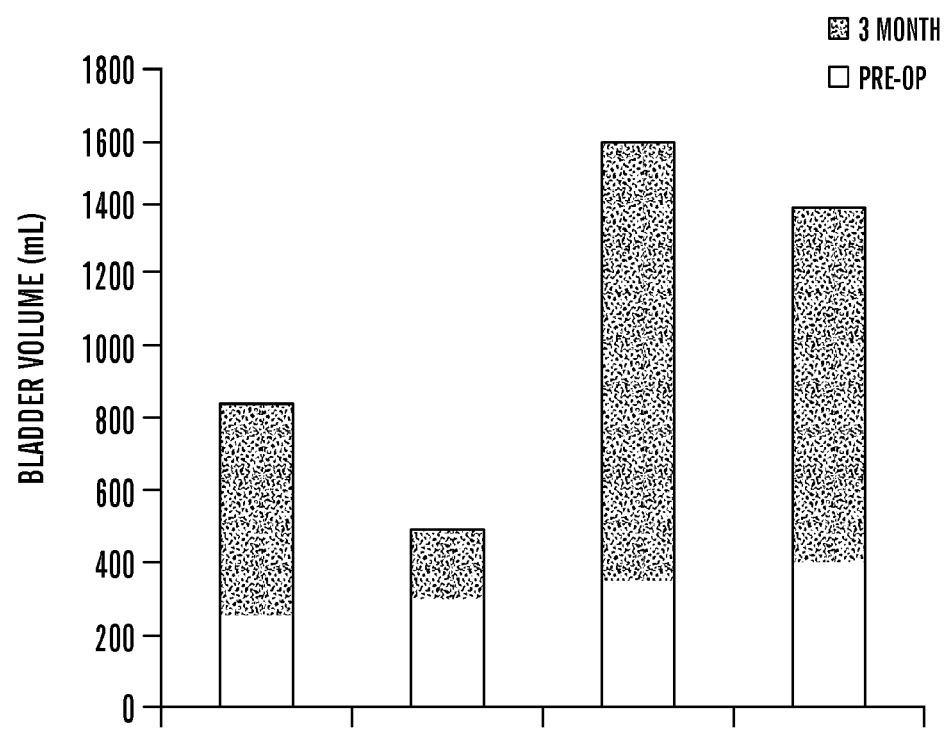
Figure 9A:
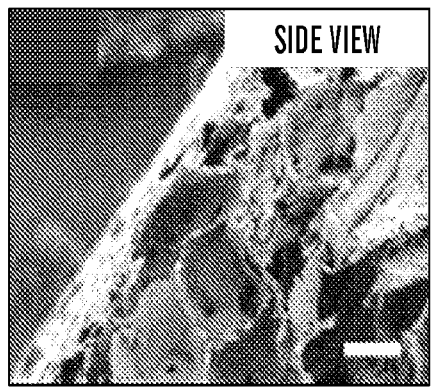
FIGS. 9A-9D depict the structural analysis of bi-layer silk scaffold and porcine bladder integration.
Figure 9B:
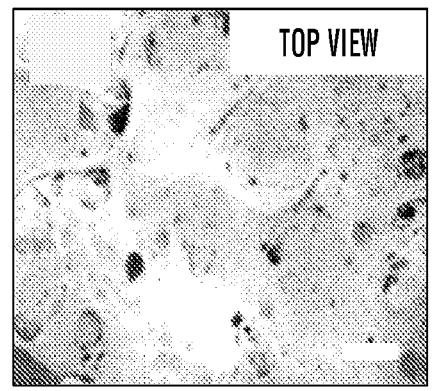
Figure 9C:
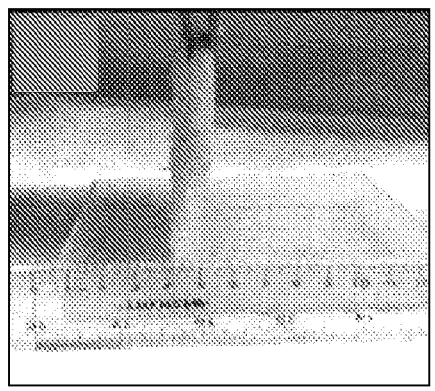
Figure 9D:
Figure 12A:
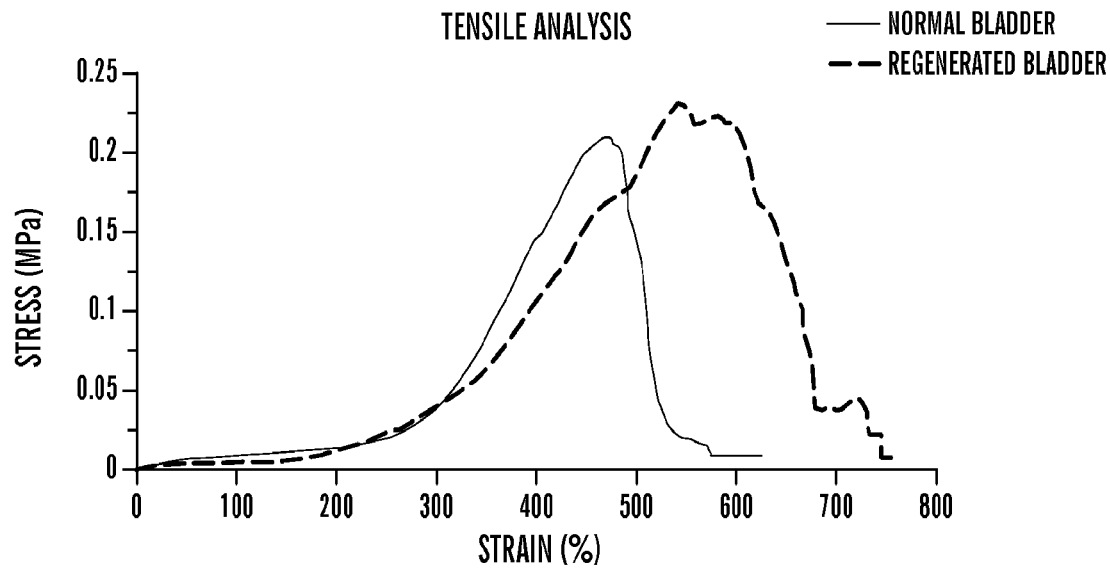
FIGS. 12A-12B depict graphs of the tensile (FIG. 12A) and functional (FIG. 12B) properties of regenerated bladder tissues.
Figure 12B:
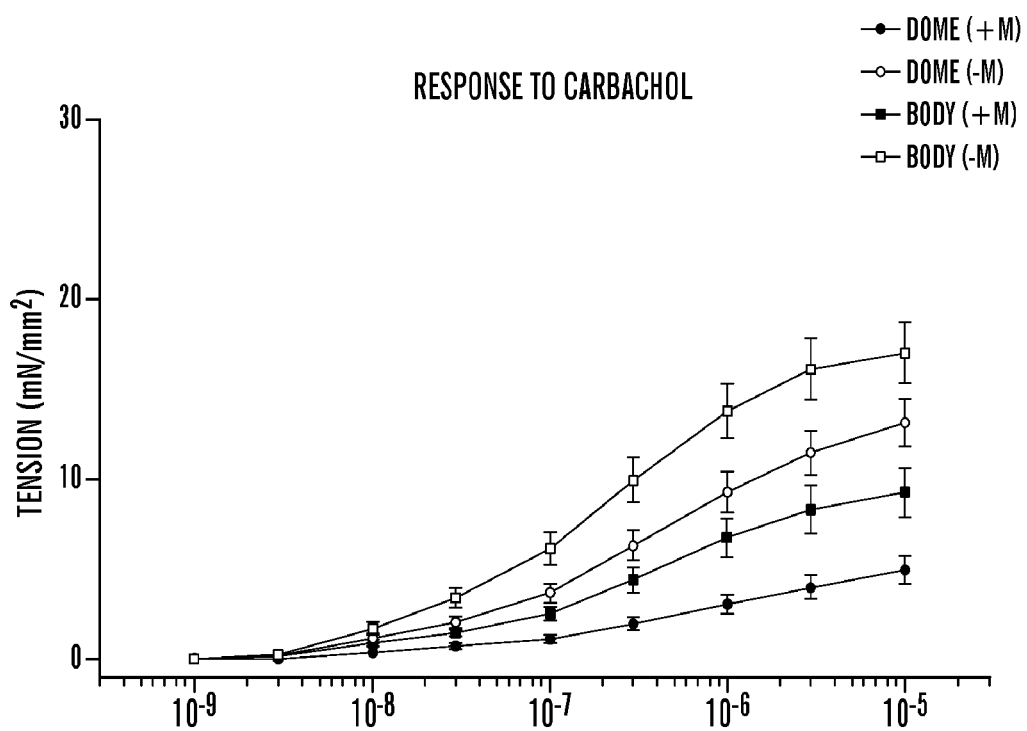

Silk augmented bladders displayed increased in capacity over time (FIGS. 8A-8B) and exhibited tensile and functional properties similar to native controls (FIGS. 12A-12B).

Acellular bi-layer silk scaffolds represent an effective biomaterial system for mediating bladder tissue regeneration and functional outcomes in a large animal model. These matrices may offer advantages over conventional gastrointestinal segments and other cellularized biomaterials for augmentation cystoplasty.

Example 4

Scaffolds (6×6 cm²) were generated from aqueous solutions of 6% silk fibroin by a previously reported solvent casting/sodium chloride-leaching process. Scanning electron microscopy (SEM) and tensile testing were performed to ascertain structural and mechanical properties of scaffolds prior to implantation. Matrices were anastomosed to the bladder dome of non-diseased Yorkshire pigs (N=2) either through open or robot-assisted augmentation cystoplasty and maintained for 3 months. Cystometric analysis was used to determine bladder capacity both pre-operatively and 3 months post-op. Following euthanasia, histological (H&E and Masson's trichrome) and immunohlstochemical (IHC) analyses of smooth muscle contractile protein expression (a-actin and SM22a) and urothelial-associated markers (cytokeratins and uroplakins) were assessed at the periphery and center of the original Implantation site as well as a nonsurgical control region.

SEM characterization of silk matrices demonstrated the formation of a bl-layer structure consisting of an internal porous network (pore size ~300 µm) buttressed on one side by a thin layer of amorphous silk (~50 µm thick) which resulted in surface pore occlusion. Tensile testing of silk scaffolds revealed an average ultimate tensile strength of 430 kPa, tensile modulus of 70 kPa, and elongation to failure of 28%. Following 1 week of Initial catheterization, animals were capable of voluntary voiding throughout the entire implantation period. Cystometric analyses of augmented bladders at 3 months post-op revealed substantial increases (>2-fold) in organ capacity in comparison to pre-operative values and weight-matched unoperated controls. Histological and IHC evaluations of both the periphery and central regions of the regenerated tissues demonstrated robust smooth muscle bundle formation displaying a-actin and SM22α expression as well as the presence of a multi-layered urothelium exhibiting both prominent uroplakin and cytokeratin positivity similar to control regions. In addition, substantial degradation of the silk matrix was noted with only discrete scaffold remnants present within the interior of the implantation site with no areas of fibrosis or stone formation observed.

Acellular bi-layer silk scaffolds represent an effective biomaterial system for mediating bladder tissue regeneration and functional outcomes in a large animal model and may offer advantages over conventional gastrointestinal segments and previously described cellularized blomaterials for augmentation cystoplasty.

Example 5

Scaffolds (6×6 cm²) were generated from 6% silk fibroin solutions using a solvent casting/sodium chloride-leaching process. Matrices were anastomosed to the bladder dome of Yorkshire pigs (N=6) and maintained for 3 months. Cystometric analysis was used to determine bladder capacity both pre-operatively and at 3 months. Regenerated tissues were evaluated by histological (H&E and Masson's trichrome) and immunohistochemical (INC) analyses of smooth muscle contractile protein expression (a-actin and SM22a), urothelial-associated markers (cytokeratins, p63, uroplakins), and markers of innervation (Fox3) and vascularization (von willebrand factor (vWF)). Nonsurgical control regions served as negative controls.

Following scaffold implantation, 5/6 swine survived to the scheduled 3 month euthanasia while 1 animal was sacrificed within the first week due to urinary ascites. Following 1 week of initial catheterization, 4/5 animals were capable of voluntary voiding throughout the entire implantation period. Cystometric analyses of augmented bladders (4/5 animals) at 3 months post-op revealed substantial increases (>2-fold) in organ capacity in comparison to pre-operative values and non surgical controls. In 4/5 animals, histological and IHC evaluations of the regenerated tissues demonstrated robust smooth muscle bundles displaying a-actin and SM22a as well as the presence of a transitional urothelium exhibiting uroplakin, p63, and cytokeratin positivity similar to control regions. Fox3 and vWF-positive cells were also observed throughout the implant site indicating de novo innervation and vascularization.

Following 1 week of initial urinary diversion via urethral catheter, animals were capable of voluntary voiding. Cystometry at 3 months revealed substantial increases (>2-fold) in bladder capacity in 5/6 augmented pigs in comparison to pre-op values and weight-matched unoperated controls. Histological and IHC evaluations of both the periphery and central regions of the regenerated tissues demonstrated robust smooth muscle formation as well as a multi-layered urothelium, similar to nonsurgical control regions. Innervation and vascularization markers were also apparent in the regenerated tissue. Regenerated tissues were evaluated by histological (H&E and Masson's trichrome) and immunohistochemical (IHC) analyses for smooth muscle contractile proteins (a-actin and SM22a), urothelial (cytokeratins, p63, uroplakins), innervation (Fox3) and vascularization (CD31) markers.

Acellular silk scaffolds represent an effective biomaterial system for mediating bladder tissue regeneration and functional outcomes in a large animal model and offer advantages over GI segments and previously described cellularized biomaterials for augmentation cystoplasty.

Example 6

Two groups of silk scaffolds were produced by a gel spinning process and consisted of either smooth, compact multi-laminates (GS1) or rough, porous lamellar-like sheets (GS2). FF silk scaffolds were produced with a solvent-casting/salt-leaching method and consisted of porous foams annealed to compact films. Bladder augmentations were performed in Sprague Dawley rats with acellular scaffolds ($7\times7$ mm$^2$) and animals were maintained for 10 weeks. Small intestinal submucosa (SIS) scaffolds were assessed in parallel while control animals received a cystotomy alone. A total of 8-10 animals per group were evaluated using cystometry, histological (H&E and Masson's trichrome), and immunohistochemical (IHC) assays at 10 weeks post-op.

Figures 10A, 10B:
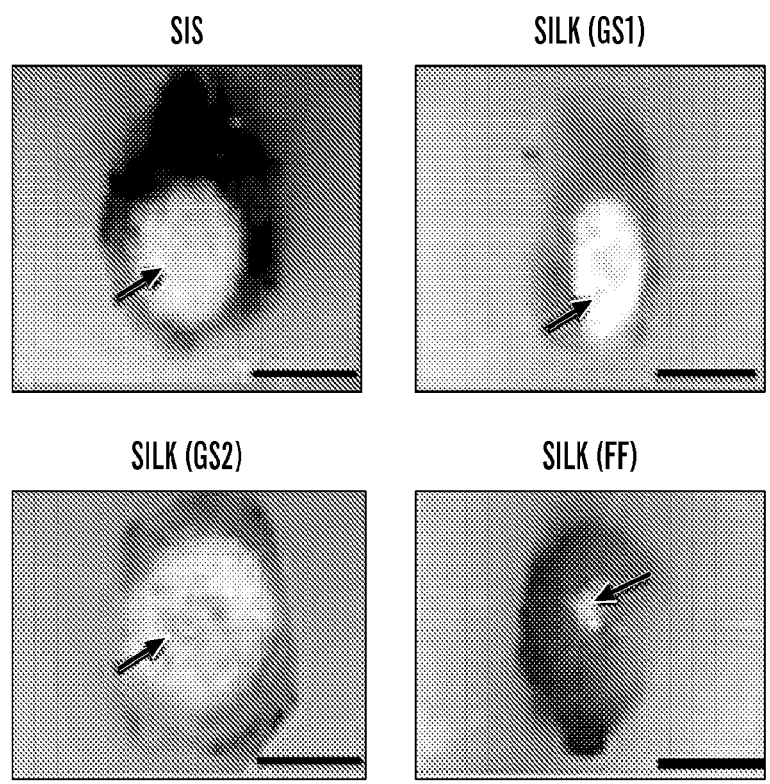
FIGS. 10A-10B depict analysis of stone formation in implants.
Figure 11A:
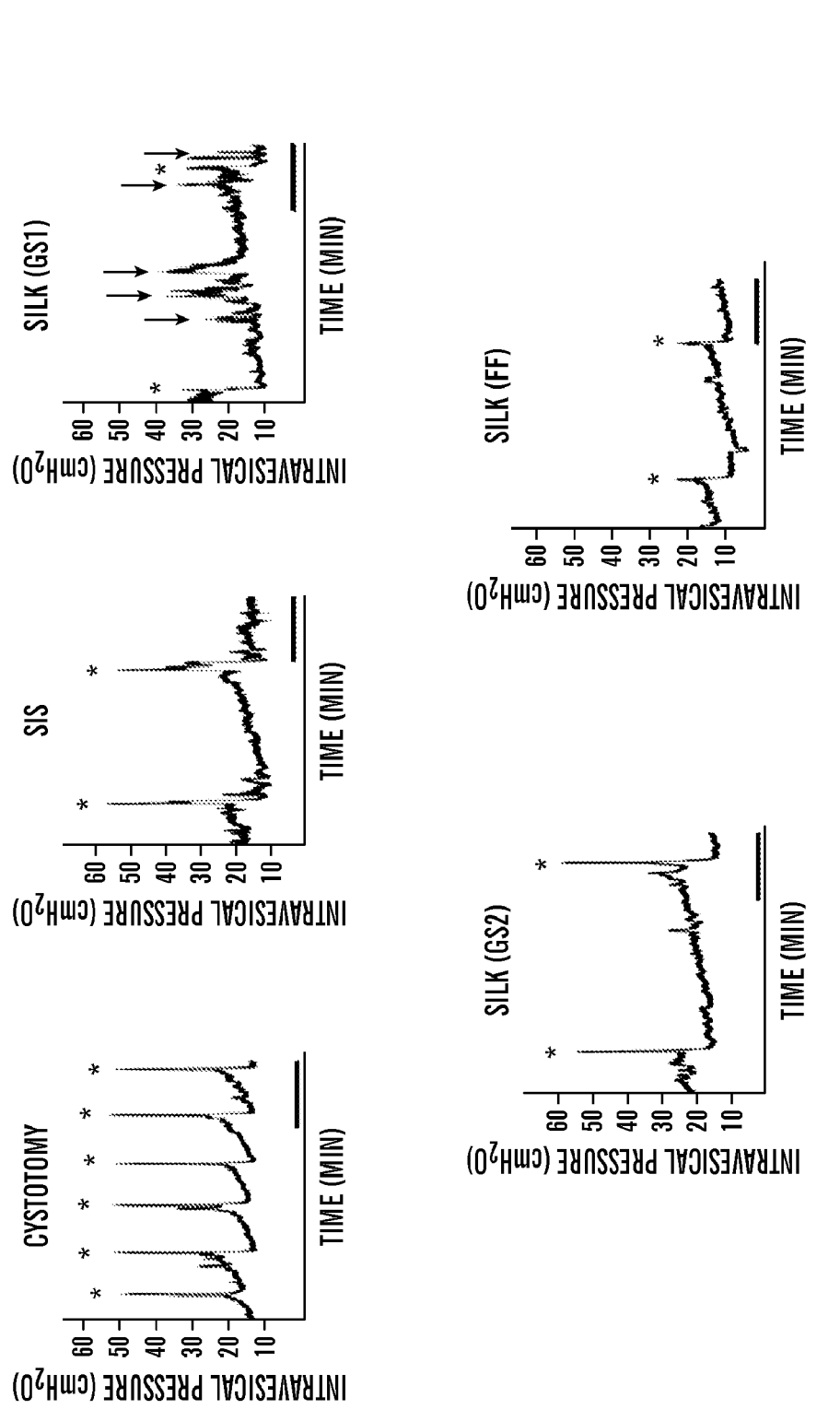

Regenerated tissues were analyzed for smooth muscle contractile protein expression (a-actin and SM22a), urothelial-associated markers (p63 and uroplakins), and markers of innervation (Fox3) and vascularization (von willebrand factor (wWF)). Robust expression of these markers within the integration site, demonstrating that the scaffold groups support innervated, vascularized smooth muscle and urothelium. Silk scaffolds support defect consolidation and the configuration influences stone formation, as shown in FIGS. 10A-10B. Additionally, silk scaffold configurations differently influence voiding function, as shown in FIGS. 11A-11B.

Variations in silk scaffold structure were demonstrated to influence the frequency of urinary stone formation with the FF group displaying a 20% incidence of stones compared to 71 and 75% rates observed in the GS1 and GS2 groups. Histological and IHC analyses demonstrated comparable extents of smooth muscle regeneration and contractile protein a-actin and SM22a) expression within the original defect sites of all groups. The regenerated tissues in each group also contained a transitional urothelium with positive uroplakin and p63 protein expression. De novo innervation and vascularization of the regenerated tissues was also confirmed in each group by robust Fox3 and CD31 protein expression. Cystometric analysis revealed significant increases in voided volumes in all groups compared to cystotomy controls. Frequency of non voiding contractions was similar in FF rats compared to controls, however the GS1 and GS2 cohorts exhibited significant overactivity, suggesting an increase in detrusor dysfunction with these matrices.

Silk scaffolds promote bladder tissue regeneration with functional voiding performance dependent on initial biomaterial fabrication techniques.

Example 7

Figure 13:
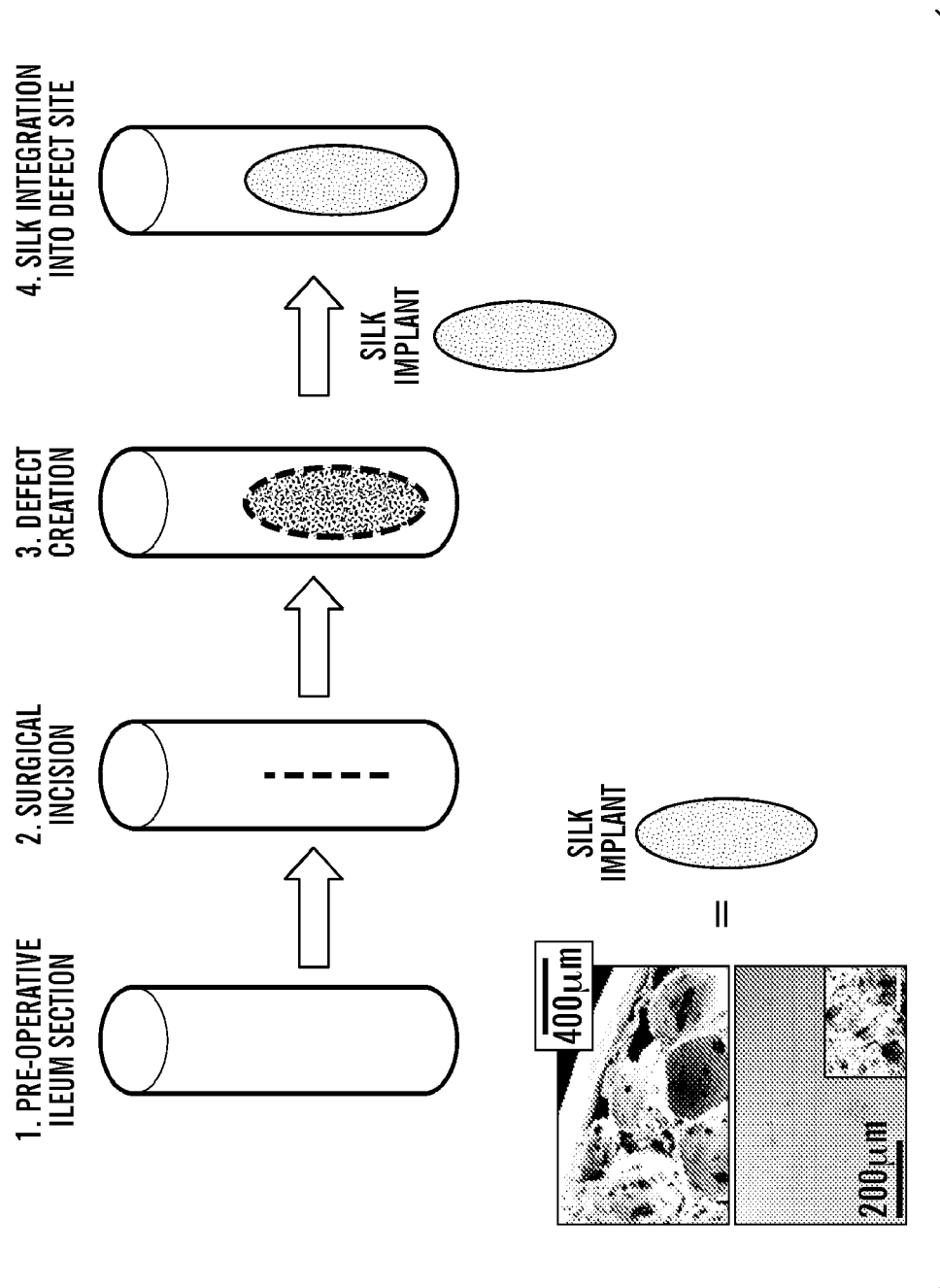
FIG. 13 depicts a schematic of the ileoplasty model in rats for Bi-layer silk implantation.
Figure 17:
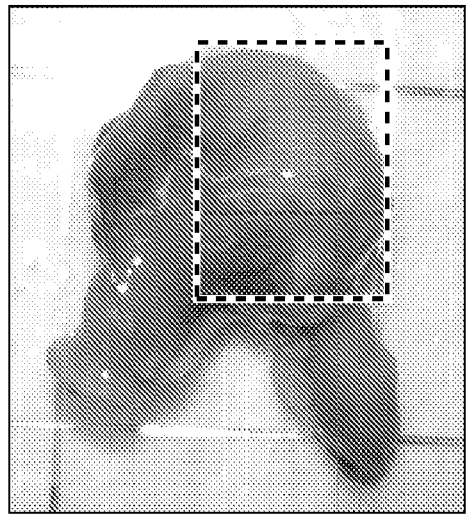
FIG. 17 depicts photographs of gross tissue observations of rat ileum implanted with bi-layer silk scaffold at 10 weeks post-implantation. Dashed boxes indicate regenerated tissue.
Figure 17:
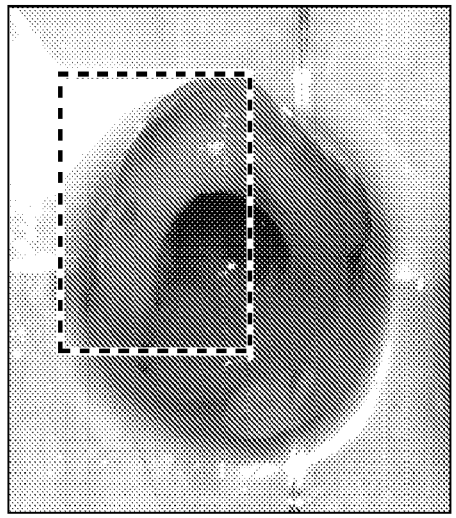
Figure 18:
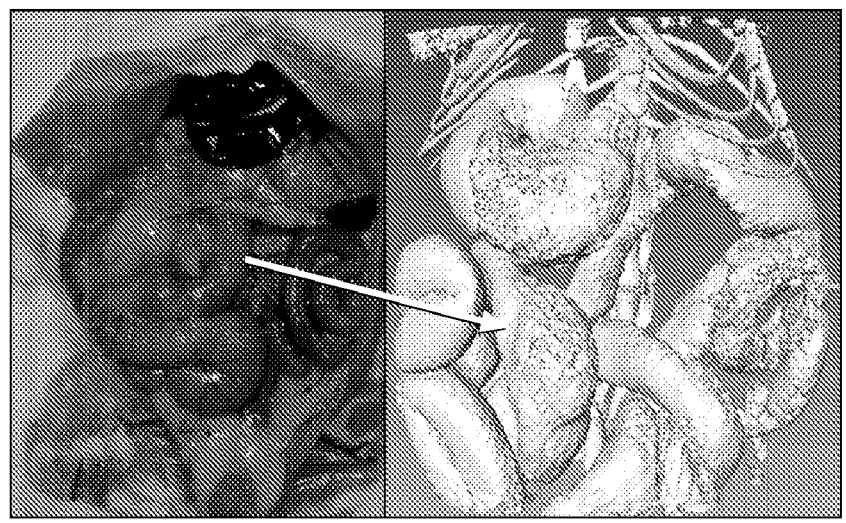
FIG. 18 depicts images of gross tissue obersvations (left panel) and microCT (right panel) of gastrointestinal tract implanted with bi-layer silk scaffold 10 weeks post-operative. The images demonstrate GI tract continuity after installation of contrast agent (ileoplasty was performed). Arrows indicate area of regenerated tissue.

The silk bilayer compositions described above herein were used to repair a surgically-created ileum defect (FIG. 13). Ileum tissue at the site of the bilayer composition implantation regenerated (FIG. 17) and demonstrated GI tract continuity by 10 weeks post-op, as determined by gross examination and microCT scan (FIG. 18). Histological and immunohistological analyses of proximal regenerated region of the ileum augmented with the bi-layer silk scaffold was performed 10 weeks post operative. Expression of smooth muscle contractile markers ($\alpha$-SMA and SM22$\alpha$) as well as epithelial markers (pancytokeratins) were observed in the regenerated tissue (data not shown).

Example 8

Silk bi-layer compositions were made according to Method 2 of Example 1, e.g. a silk fibroin foam was cast while in contact with a pre-existing silk fibroin film, and used to regenerate porcine bladder tissue.

Figure 14:
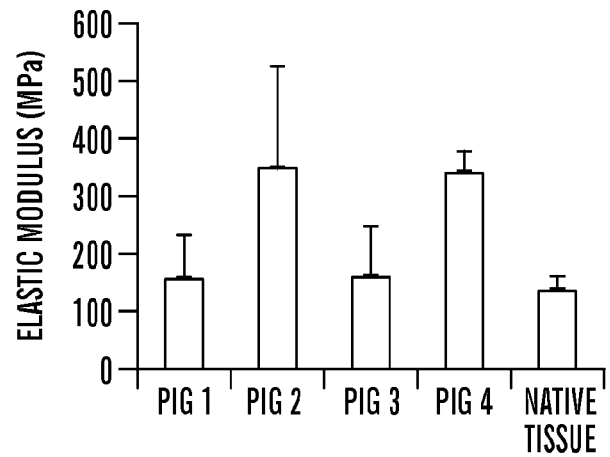
FIG. 14 depicts graphs of tensile testing analyses of regenerated and native procine bladder tissues performed to assess mechanical stress.
Figure 14:
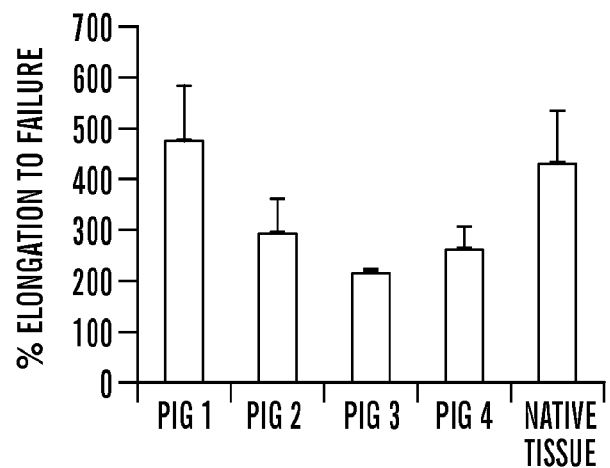
Figure 14:
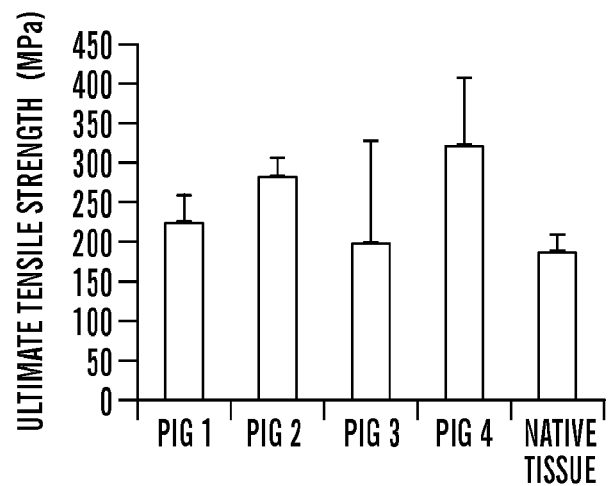
Figure 14:

Methods: Matrices were anastomosed to the bladder dome of Yorkshire pigs (N=4) either through open augmentation cystoplasty, and after an initial catheter drainage period of 7 days, were maintained for 3 months. Cystometric analysis was used to determine bladder capacity both pre-operatively and 3 months post-op (Table 1). Following euthanasia, histological (H&E) and immunohistochemical (IHC) analyses of smooth muscle contractile protein expression (a-actin and SM22a), urothelial-associated markers (cytokeratins, p63, and uroplakins), and markers of innervation (synaptophysin) and vascularization (CD31) were assessed at the periphery and center of the original implantation site as well as a nonsurgical control region. Marker expression indicated smooth muscle and urothelial regeneration as well as vascularization and innervation in the implant area. Tensile testing analyses of regenerated and native porcine bladder tissue was performed to assess mechanical properties (FIG. 14). Regenerated tissue perfomed, on average, similarly to native tissue.

TABLE 1

Bladder capacity (capacity at 20 cm H2O) pre-operatively and at 3 months after augmentation with silk scaffold.

| Animal Replicates | Pre-operative bladder capacity (ml) | 3 month bladder capacity (ml) |
|---|---|---|
| Pig 1 | 358 | 1000 |
| Pig 2 | 1000 | 1600 |
| Pig 3 | 450 | 1600 |
| Pig 4 | 850 | 1600 |

Example 9

B. mori silkworm cocoons were boiled for 20 min in an aqueous solution of 0.02M Na2CO3 and then rinsed thoroughly with distilled water to extract the glue-like sericin proteins and wax. The extracted silk fibroin was then dissolved in 9.3M LiBr solution at 60 C for 6 h. This solution was dialyzed in distilled water using a Slide-a-lyzer dialysis cassette (MWCO, 3500) for 4 d yielding an 8% (wt/vol) aqueous silk fibroin solution. 75 ml of an aqueous silk fibroin solution (6% wt/vol) was poured into a rectangular casting vessel (12 cm×10 cm) and granular NaCl (150 g, 500-600 μM average crystal size) mixed with the silk solution. The resultant solution was allowed to cast for 2 d at room temperature and then NaCl was removed by washing in distilled water for 2 d. Spontaneous formation of the bi-layer scaffold was achieved with random pore occlusion occurring at the bottom of the matrix plane adjacent to the face of the casting vessel. For implantation, the porous compartment can be trimmed in thickness to allow for the total bi-layer scaffold thickness to approximate the thickness of the surrounding host tissue. The area of the scaffold was also trimmed to accommodate the defect area.

Example 10

Figure 19A:
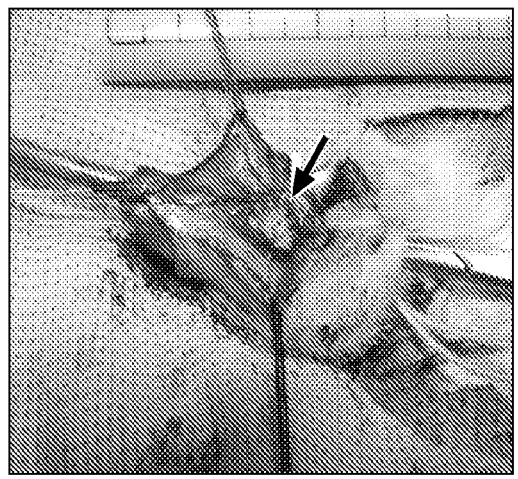
FIGS. 19A-19B demonstrate that silk scaffolds support urethral continuity following onlay urethroplasty in rabbits.
Figure 19B:
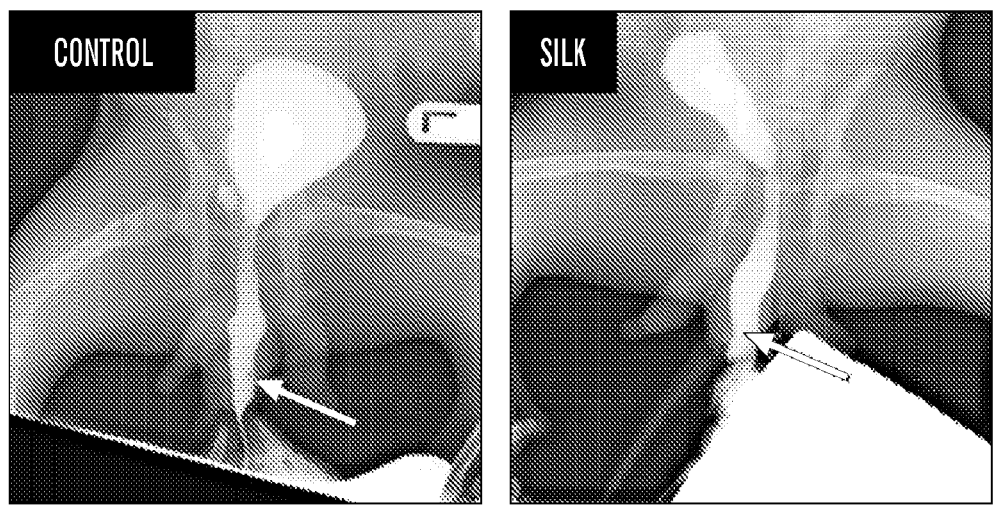

FIGS. 19A-19B demonstrate that silk scaffolds support urethral continuity following onlay urethroplasty in rabbits. FIG. 19A depicts an image of the model of surgical procedure and silk implantation within rabbit urethra. FIG. 19B depicts retrograph urethrograms demonstrating no reduction in urethral caliber or stricture formation following 3 months of silk implantation. Controls represent urethras which were surgically incised, claosed, and maintained in parallel with silk implanted animals. Results are representative of N=2 animals performed with silk implants as well as controls. Arrows denote original implantation site or sham injury.

What is claimed herein is:

1. A multilayer biomaterial composition, comprising:
    a first and second layer;
        the first layer comprising a porous biomaterial matrix, wherein the porous biomaterial matrix comprises silk fibroin, and
        the second layer comprising an impermeable biomaterial layer, wherein the impermeable biomaterial layer is characterized in that it prevents passage of liquid water across it,
    wherein a bottom surface of the second layer contacts and/or covers a top surface of the first layer,
    wherein the multilayer biomaterial composition has a shape selected from the group consisting of approximately a contoured sheet, a plane, a cuboid a sheet, and a tube, so that the multilayer biomaterial composition, when positioned at a site of a wound or defect, a bottom surface of the first layer is oriented such that the porous biomaterial matrix of the first layer is in contact with the wound or defect and provides a scaffold for tissue regeneration and the impermeable biomaterial layer provides a seal that prevents passage of cellular material, fluids, hollow organ contents, and/or particles into the site.

2. The composition of claim 1, wherein the matrix is a structure selected from the group consisting of: foams; hydrogels; electrospun fibers; gels; fiber mats; sponges; 3-dimensional scaffolds; non-woven mats; woven materials; knit materials; fiber bundles; and fibers.

3. The composition of claim 1, wherein the biomaterial of the impermeable biomaterial layer is selected from the group consisting of: silk fibroin; PGA; collagen; polyethylene oxide, fibronectin, keratin, polyaspartic acid, polylysin, alginate, chitosan, chitin, and hyaluronic acid.

4. The composition of claim 1, wherein the first and second layers comprise silk fibroin.

5. The composition of claim 1, wherein the second layer comprises a biomaterial that is not silk fibroin.

6. The composition of claim 1, further comprising an agent.

7. The composition of claim 1, wherein the average pore size of the porous silk fibroin matrix is at least 200 μm.

8. The composition of claim 1, wherein the average pore size of the porous silk fibroin matrix is from about 200 μm to about 600 μm.

9. The composition of claim 1, wherein the impermeable biomaterial layer is from about 10 μm to about 600 μm thick.

10. The composition of claim 1, wherein the composition is from about 0.01 cm to about 5 cm thick.

11. The multilayer biomaterial composition of claim 1, wherein the wound or defect is a hollow organ wound or defect.

12. The multilayer biomaterial composition of claim 11, wherein the hollow organs include a bladder; a portion of a gastrointestinal tract; a stomach; and/or intestines.

13. The multilayer biomaterial composition of claim 12, wherein the portion of the gastrointestinal tract is an esophagus.

14. The multilayer biomaterial composition of claim 1, when positioned at site of wound or defect, the composition is sutured.

15. The multilayer biomaterial composition of claim 1, wherein the composition is characterized by an elastic modulus up to about 2.7 MPa.

16. The multilayer biomaterial composition of claim 1, wherein the composition is characterized by an extensibility between about 25% and about 500%.

17. The multilayer biomaterial composition of claim 1, wherein the shape is the contoured sheet is curved, arced, or angled such that it matches a contour of tissue to be regenerated.

18. The multilayer biomaterial composition of claim 1, wherein an edge of the impermeable biomaterial layer extends beyond the porous biomaterial matrix.

19. The multilayer biomaterial composition of claim 1, wherein the impermeable biomaterial layer is annealed.

20. The composition of claim 1, wherein the second layer comprises an impermeable layer of silk fibroin.

21. A method of producing a composition of claim 1, the method comprising;
    contacting a porous biomaterial matrix with an impermeable biomaterial layer, wherein the porous biomaterial matrix comprises silk fibroin.

22. The method of claim 21, wherein the method further comprises adding an agent to at least one layer.

23. The method of claim 22, wherein the agent is a therapeutic agent.

24. A method of producing a composition of claim 1, the method comprising;
    (a) casting an admixture of aqueous biomaterial solution and NaCl, wherein the aqueous biomaterial solution comprises silk fibroin;
    (b) contacting the composition resulting from step (a) with water.

25. The method of claim 24, wherein step (a) is performed with the solution in contact with a pre-existing impermeable biomaterial layer.

26. The method of claim 24, wherein the admixture is cast for from about 12 hours to about 96 hours.

27. The method of claim 24, wherein step (b) proceeds for from about 12 hours to about 120 hours.

28. The method of claim 24, wherein the water is removed and replaced with a fresh volume of water at least once during step (b).

29. The method of claim 24, wherein, during the casting step, the admixture of biomaterial solution and NaCl is in contact with an impermeable biomaterial layer.

* * * * *